Figure 1:
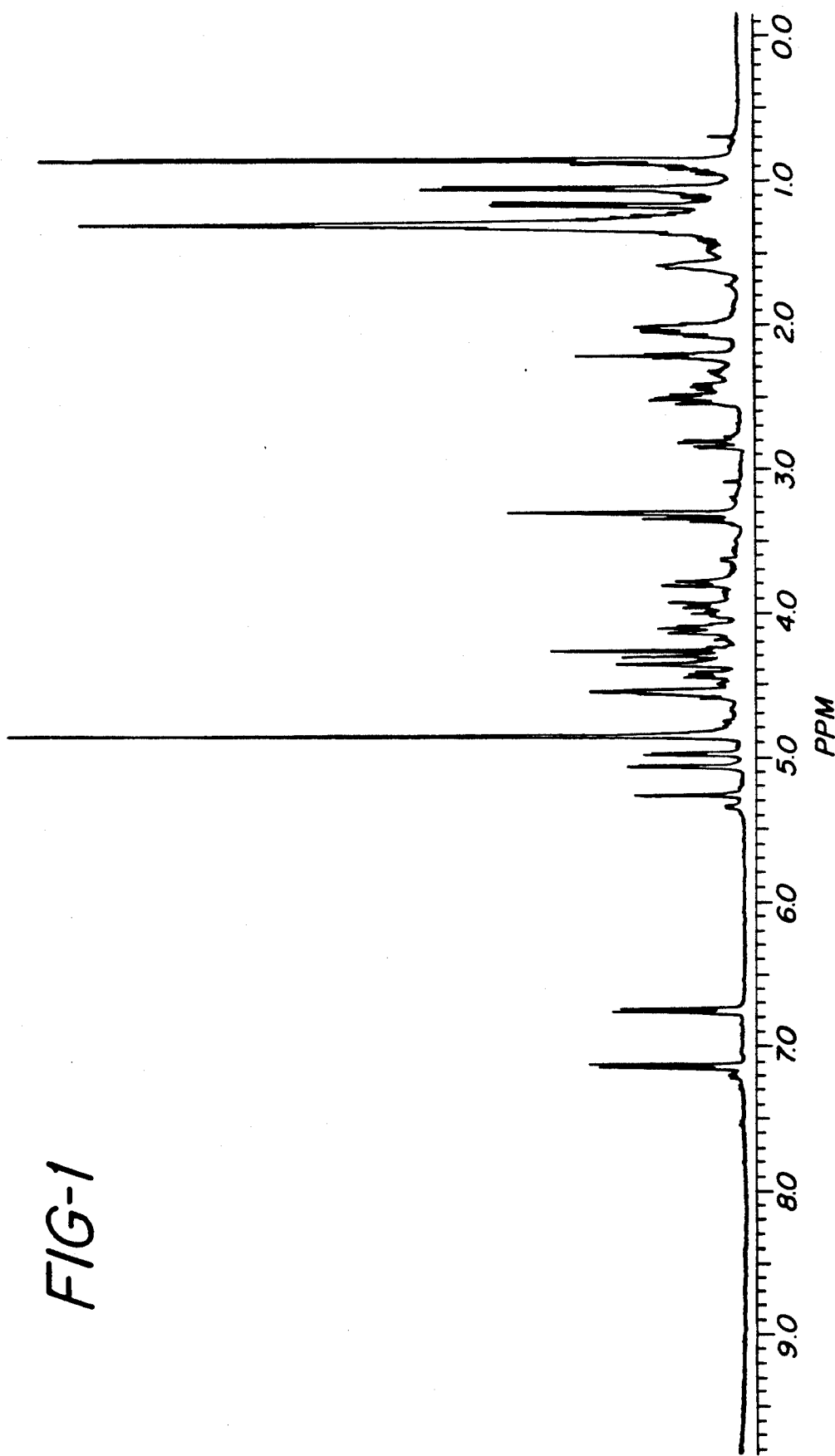

United States Patent [19]
Schmatz

[11] Patent Number: 5,166,135
[45] Date of Patent: * Nov. 24, 1992

[54] METHOD FOR THE CONTROL OF PNEUMOCYSTIS CARINII

[75] Inventor: Dennis M. Schmatz, Cranford, N.J.

[73] Assignee: Merck & Company, Inc., Rahway, N.J.

[*] Notice: The portion of the term of this patent subsequent to Jun. 5, 2007 has been disclaimed.

[21] Appl. No.: 743,473

[22] Filed: Aug. 9, 1991

Related U.S. Application Data

[63] Continuation-in-part of Ser. No. 398,889, Aug. 30, 1989, abandoned, which is a continuation-in-part of Ser. No. 242,767, Sep. 12, 1988, abandoned, and a continuation-in-part of Ser. No. 246,042, Sep. 16, 1988, abandoned.

[51] Int. Cl.$^5$ .............................................. A61K 37/00
[52] U.S. Cl. ..................................... 514/11; 530/317; 530/318
[58] Field of Search ............... 514/9, 10, 11; 530/317, 530/318

[56] References Cited

U.S. PATENT DOCUMENTS

| | | | |
|---|---|---|---|
| 3,978,210 | 8/1976 | Mizuno et al. | 424/118 |
| 4,024,245 | 5/1977 | Hoehn et al. | 424/119 |
| 4,024,246 | 5/1977 | Higgens et al. | 424/119 |
| 4,173,629 | 11/1979 | Dreyfuss et al. | 424/118 |
| 4,287,120 | 9/1981 | Abbott et al. | 530/317 |

(List continued on next page.)

FOREIGN PATENT DOCUMENTS

| | | |
|---|---|---|
| 851310 | 10/1977 | Belgium . |
| 859067 | 3/1978 | Belgium . |
| A10032009 | 7/1981 | European Pat. Off. . |
| A30311194 | 4/1989 | European Pat. Off. . |
| A20311193 | 12/1989 | European Pat. Off. . |
| 2803581 | 2/1979 | Fed. Rep. of Germany . |
| 2050385A | 2/1980 | United Kingdom . |

OTHER PUBLICATIONS

Hughes, W. T., Eur. J. Epidemid 5(3), 265-9 (Sep. 1989).
Hughes, W. T. Index Medicus.
Benz et al., Helv. Chim. Acta 57, 8, 2459-77 (1974).

(List continued on next page.)

*Primary Examiner*—C. Warren Ivy
*Assistant Examiner*—Celia Chang
*Attorney, Agent, or Firm*—Alice O. Robertson; Raymond M. Speer

[57] ABSTRACT

A method for the treatment of *Pneumocystis carinii*, the causative agent of pneumonia of particular severity to immune compromised patients such as those with acquired immune deficiency syndrome (AIDS), by administering a lipophilic cyclohexapeptide compound of the general formula

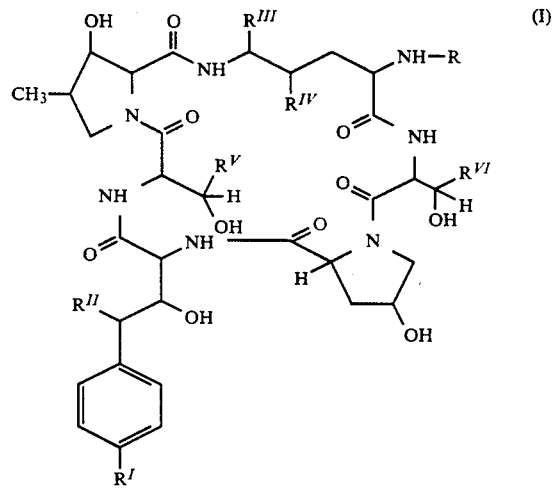

(I)

wherein the R groups are fully defined in the text, is described. Compositions suitable for the treatment of *P. carinii* are also disclosed.

16 Claims, 2 Drawing Sheets

U.S. PATENT DOCUMENTS

| | | | |
|---|---|---|---|
| 4,288,549 | 9/1981 | Boeck et al. | 435/119 |
| 4,293,482 | 10/1981 | Abbott et al. | 530/317 |
| 4,293,483 | 10/1981 | Debono | 530/317 |
| 4,293,485 | 10/1981 | Debono | 530/317 |
| 4,293,487 | 10/1981 | Debono | 530/317 |
| 4,293,488 | 10/1981 | Debono | 530/317 |
| 4,293,489 | 10/1981 | Debono | 530/317 |
| 4,293,490 | 10/1981 | Abbott et al. | 530/317 |
| 4,293,491 | 10/1981 | Debono | 530/317 |
| 4,299,762 | 11/1981 | Abbott et al. | 530/317 |
| 4,299,763 | 11/1981 | Abbott et al. | 530/317 |
| 4,304,716 | 12/1981 | Abbott et al. | 530/317 |
| 4,320,053 | 3/1982 | Abbott et al. | 530/317 |
| 4,320,054 | 3/1982 | Abbott et al. | 530/317 |
| 4,322,338 | 3/1982 | Abbott et al. | 530/317 |
| 4,814,323 | 3/1989 | Andrieu et al. | 514/11 |
| 4,835,140 | 5/1989 | Smith et al. | 514/24 |
| 4,931,352 | 6/1990 | Fromtling et al. | 514/11 |
| 5,021,403 | 6/1991 | Sesin et al. | 514/9 |
| 5,049,546 | 9/1991 | Sesin et al. | 514/9 |

OTHER PUBLICATIONS

Traber et al., Helv. Chim. Acta 62, 4, 1252–67 (1979).
Roy et al., J. Antibiotics, XL, 3, 275–80 (1987).
Mukhopadhyay et al., J. Antibiotics, XL, 3, 281–289 (1987).
Gordee et al., J. Antibiotics XXXVII, 9, 1054–65 (1984).
Schwartz, R. E. et al., J. Antibiotics, 42, No. 2, 163 (1989).
Wichmann, C. F. et al., J. Antibiotics, 42, No. 2, 168 (1989).
Fromtling, R. A. et al., J. Antibiotics, 42, No. 2, 174 (1989).
Pache, W. et al., 13th International Congress Chemotherapy (1983), PS 4.8/3, Part 115, Abstract No. 10; also referenced in Ann. Reports in Med. Chem. 19, Sec. III, 130–131.
CRC Handbook of Antibiotic Compound, vol. IV, Part I pp. 355–367.

METHOD FOR THE CONTROL OF PNEUMOCYSTIS CARINII

This is a continuation-in-part of copending application Ser. No. 398,889, filed Aug. 30, 1989, now abandoned which in turn is a continuation-in-part of copending applications Ser. No. 242,767, field Sep. 12, 1988, now abandoned and Ser. No. 246,042, filed Sep. 16, 1988, now abandoned.

BACKGROUND OF THE INVENTION

*Pneumocystis carinii* is an opportunistic organism which is widely prevalent but generally dormant until bodily defenses of the host are compromised whereupon it propagates in the host causing disease. Generally it is present in the lungs although extrapulmonary infections have been reported. Lung infections with this organism in immunocompromised individuals generally lead to pneumonia and are usually fatal if untreated. It has been suggested that patient to patient transmission also may occur in immunocompromised individuals. The immunocompromised state of individuals is usually associated with genetic defects, lymphoproliferative diseases, or with conditions resulting from cancer therapy, or treatment with immunosuppressive drugs, or as a consequence of AIDS. Most AIDS patients eventually contract *Pneumocystis carinii* pneumonia (PCP) and have accounted for the majority of the recent cases of this disease. Left untreated, PCP is almost always fatal.

The current method of treatment for *P. carinii* pneumonia is trimethoprim/sulfamethoxazole or pentamidine. Treatment with trimethoprim/sulfamethoxazole (TMP/SMZ) is associated with a high level of toxic side effects including rash, elevated liver function, nausea and vomiting, anemia, creatine elevation, and in extreme cases, Stevens-Johnson syndrome. Side effects from TMP/SMZ are much more prevalent in patients with AIDS. Treatment with pentamidine is also associated with a high level of toxic side effects including renal failure, hepatotoxicity, hypoglycemia, hematologic abnormalities and pain or abscess at the injection site. The mortality due to treatment can reach 20 to 30 percent. An improved method for the treatment of *P. carinii* pneumonia in immune-compromised patients is greatly needed.

DESCRIPTION OF THE INVENTION

The present invention is directed to a method for treatment or prevention of *Pneumocystis carinii* infections in mammals which comprises administering to subjects, a person or animal, infected with or susceptible to being infected with *Pneumocystis carinii*, an anti-infection or infection controlling amount of a cyclohexapeptide compound.

The compounds within the scope of the present invention include a novel fungal metabolite as hereinafter detailed, known echinocandin type of antibiotics which are lipophilic cyclohexapeptides having a fatty acid side chain, simple derivatives of the echinocandin type antibiotics such as side chain dihydro- and tetrahydro- reduction products, ring ether derivatives and semi-synthetic products in which the cyclohexapeptide ring is retained but in which the fatty acid side chain is replaced. Most of the compounds described in the literature are taught to be antifungal agents.

The compounds suitable for the practice of the present invention which include not only natural antibiotic compounds but also simple derivatives of natural antibiotic compounds and semi-synthetic compounds as are hereinafter fully detailed may be represented by the formula (I).

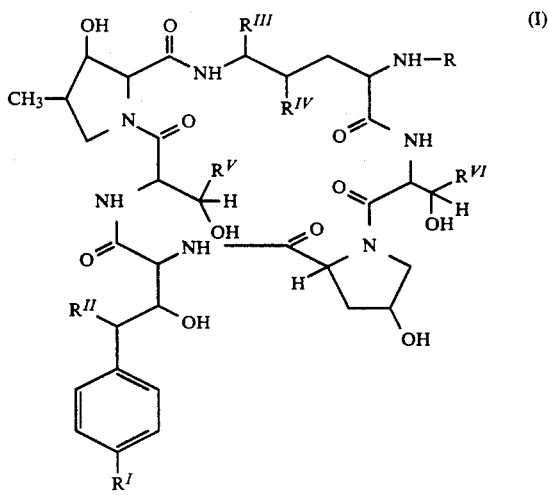

In this and succeeding formulas
$R^I$ is H or OH;
$R^{II}$ is H or OH;
$R^{III}$ is H, OH, —O-alkyl($C_1$–$C_6$), —O-benzyl, or

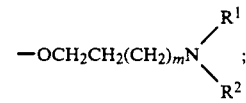

wherein $R^1$ is H, $C_1$–$C_6$ alkyl, $C_3$–$C_7$ cycloalkyl, hydroxyethyl, lower alkoxyethyl, furylmethyl, tetrahydrofurylmethyl, phenyl, phenylalkyl wherein the phenyl may be substituted with halo, hydroxy, lower alkyl and lower alkoxy; $R^2$ is hydrogen or lower alkyl; or $R^1$ and $R^2$ together form —$(CH_2)_2Q(CH_2)_2$— wherein Q is a connecting group such as —$CH_2$—, —NH— or —N-(lower alkyl)—; and m is from 0 to 4;
$R^{IV}$ is H or OH;
$R^V$ is H, $CH_3$ or $CH_2CONH_2$; and
$R^{VI}$ is H or $CH_3$ R is (A) $-\overset{O}{\underset{\|}{C}}$-alkyl, from 6 to 24 carbon atoms, (B) $-\overset{O}{\underset{\|}{C}}$-alkenyl, from 6 to 24 carbon atoms, (C)

(i) 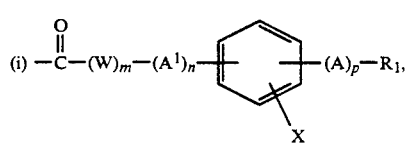

-continued

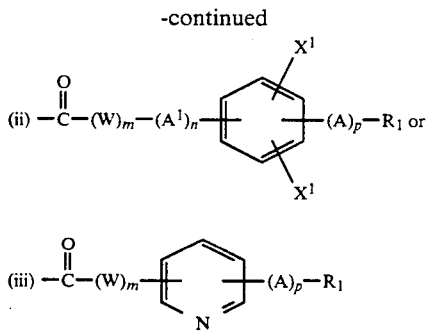

when $R^I$, $R^{II}$, $R^{III}$ and $R^{IV}$ are OH and $R^V$ and $R^{VI}$ are $CH_3$;

wherein in said (i), (ii) or (iii),

A is a divalent oxygen, sulfur, sulfinyl or sulfonyl;

$A^1$ is divalent oxygen, sulfur, sulfinyl, sulfonyl or —NH—;

X is hydrogen, chloro, bromo, iodo, nitro, $C_1$-$C_3$ alkyl, hydroxy, $C_1$-$C_3$ alkoxy, mercapto, $C_1$-$C_3$ alkylthio, carbamyl or $C_1$-$C_3$ alkylcarbamyl;

$X^1$ is chloro, bromo or iodo;

$R_1$ is hydrogen, $C_1$-$C_{18}$alkyl or $C_2$-$C_{18}$alkenyl;

W is $C_1$-$C_{10}$alkylene or $C_2$-$C_{10}$alkenylene; m, n and p are 0 or 1, but when m is 0, n is 0;

provided that the sum of the carbon atoms in the $R_1$ and W groups must be greater than 4 but cannot exceed 21; that when X is mercapto A and $A^1$ cannot be sulfinyl or sulfonyl; and that when A and $A^1$ are sulfinyl or sulfonyl, they must be in equal oxidation states;

(D) when $R^I$ is OH, $R^{II}$ $R^{III}$ and $R^{IV}$ are H, then

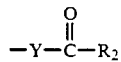

wherein Y is a divalent aminoacyl radical of the formula

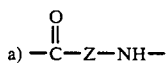

wherein Z is $C_1$-$C_{10}$alkylene or $C_5$-$C_6$cycloalkylene

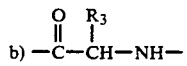

wherein $R_3$ is hydroxymethyl, hydroxyethyl, mercaptomethyl, mercaptoethyl, methylthioethyl, 2-thienyl, 3-indolomethyl, phenyl, benzyl, halophenyl, halobenzyl, $C_1$-$C_3$ alkylphenyl, $C_1$-$C_3$ alkylbenzyl, $C_1$-$C_3$ alkylthiophenyl, $C_1$-$C_3$ alkylthiobenzyl, carbamylphenyl, carbamylbenzyl, $C_1$-$C_3$ alkylcarbamylphenyl or $C_1$-$C_3$ alkylcarbamylbenzyl; or

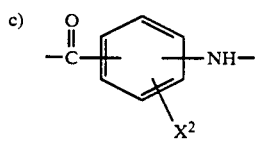

wherein $X^2$ is hydrogen or halo; and $R_2$ is $C_1$-$C_{17}$ alkyl and $C_2$-$C_{17}$ alkenyl.

The preferred compounds are those having the following substituents in formula (I):

$R^I$ is OH;

$R^{II}$ is H or OH;

$R^{III}$ is H, OH, —O-alkyl($C_1$-$C_6$), —O-benzyl, or

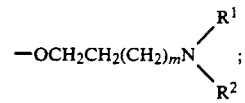

wherein $R^1$ is H, $C_1$-$C_6$ alkyl, $C_3$-$C_7$ cycloalkyl, preferably $C_5$-$C_6$ cycloalkyl, hydroxyethyl, ($C_1$-$C_4$ alkoxy)ethyl; $R^2$ is hydrogen or ($C_1$-$C_4$ alkyl); or $R^1$ and $R^2$ together form —$(CH_2)_5$—, and m is from 0 to 4;

$R^{IV}$ is H or OH, preferably OH;

$R^V$ is H, $CH_3$ or $CH_2CONH_2$;

$R^{VI}$ is H or $CH_3$; and

R is (A) $-\overset{O}{\underset{\|}{C}}$-alkyl, preferably from 6 to 24 carbon atoms, (B) $-\overset{O}{\underset{\|}{C}}$-alkenyl, preferably from 6 to 24 carbon atoms, or

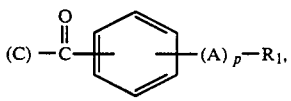

wherein in said (C),

A is divalent oxygen or sulfur;

$R_1$ is hydrogen, $C_1$-$C_{18}$alkyl or $C_2$-$C_{18}$alkenyl; p is 0 or 1; provided that $R^{I-IV}$ are OH and $R^V$ and $R^{VI}$ are $CH_3$.

The term "alkyl" is meant a univalent saturated straight chain or branched chain hydrocarbon radical. The term "alkenyl" is meant an univalent, unsaturated, straight chain or branched chain hydrocarbon radical containing not more than three double bonds. By "lower" is meant up to 6 carbon atoms. The term "halo" is meant chloro, bromo, fluoro and iodo.

The compounds useful in the method of treatment for or prevention of *Pneumocystis carinii* infections in mammals according to the present invention are generally white crystalline or powdery substances. They are generally of good solubility in alcohols such as methanol and ethanol, of poor solubility in water and in hydrocarbons such as hexane and of intermediate solubility in many common solvents. The solubility properties as well as other properties of many of the naturally occurring cyclohexapeptides are summarized in the CRC Handbook of Antibiotic Compounds, Vol IV, Part I, pp. 355-367, *CRC Press, Inc. Boca Raton*, Fla., 1980.

An especially preferred compound is a novel fungal metabolite in which $R^I$, $R^{II}$, $R^{III}$ and $R^{IV}$ are OH, $R^V$ is —$CH_2CONH_2$, $R^{VI}$ is $CH_3$ and R is

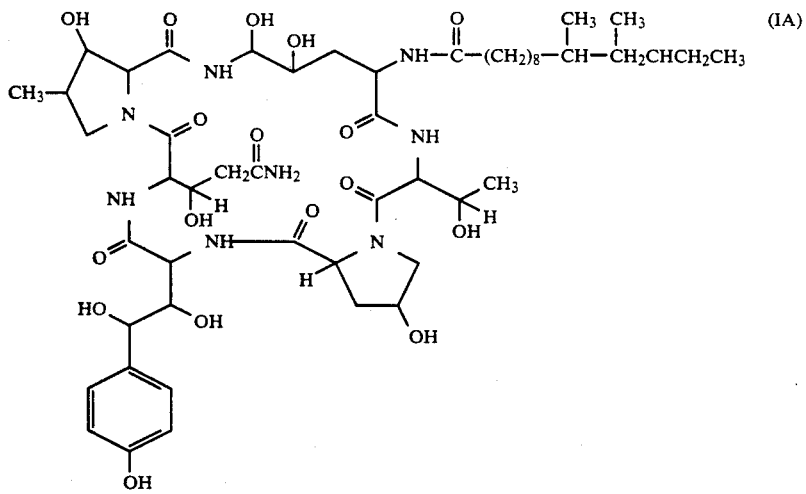

The compound may be named 1-[4,5-dihydroxy-$N^2$-(10,12-dimethyl-1-oxotetradecyl)-L-ornithine-5-(threo-3-hydroxy-1-glutamine)echinocandin B but hereinafter, for convenience, will be referred to as Compound IA. Especially preferred is the isomer which may be named 1-[(4R,5R)-4,5-dihydroxy-$N^2$-(10,12-dimethyl-1-oxo-tetradecyl)-L-ornithine-5-(threo-3-hydroxy-1-glutamine)echinocandin B. The preparation and properties of Compound IA are hereinafter described and are also the subject of copending applications Ser. No. 105,795, filed Oct. 7, 1987, which was abandoned in favor of copending application Ser. No. 362,647, filed Jun. 7, 1989 now U.S. Pat. No. 4,931,352, Jun. 5, 1990; and Ser. No. 105,797, filed Oct. 7, 1987, now U.S. Pat. No. 4,968,604, Nov. 6, 1990.

Compound IA, the preferred compound, is a white solid which may be characterized by the following physical properties:

a decomposition temperature of 206°–214° C.;

an empirical formula of $C_{51}H_{82}N_8O_{17}$ determined by high resolution FAB (Fast Atom Bombardment mass spectrometric measurement, calculated for $C_{51}H_{82}N_8O_{17}$ +Li=1085.5958, found=1085.6146);

an amino acid composition as determined by gas chromatogram/mass spectra of the trimethylsilyl derivative of the total acid hydrolysates of one equivalent each of threonine, hydroxyproline, methylhydroxyproline, and hydroxyglutamic acid.

$^1$H NMR Spectra in CD$_3$OD at 400 MHz as seen in FIG. 1; and $^{13}$C NMR chemical shifts obtained in CD$_3$OD at 100 MHz as follows: 11.20, 11.64, 19.75, 20.25, 20.78, 27.00, 28.07, 30.33, 30.37, 30.61, 30.76, 31.19, 31.29, 32.94, 34.83, 36.69, 38.10, 38.54, 39.07, 39.53, 45.93, 51.39, 53.01, 55.59, 56.31, 57.11, 58.35, 62.43, 68.18, 70.08, 70.55, 70.61, 71.26, 73.94, 75.72, 75.84, 76.86, 116.06(×2), 129.43(×2), 132.86, 158.22, 168.80, 172.16, 172.35, 172.40, 173.12, 174.24, 175.47, 176.88 ppm.

The compound is soluble in a variety of organic solvents such as methanol, ethanol, dimethylformamide, dimethyl sulfoxide, and the like.

The production of Compound IA, a novel compound, is described hereinafter in detail. The other compounds useful in the present invention may be prepared in a similar manner by substituting an appropriate microorganism or by other procedures as subsequently described.

Compound IA may be produced by cultivating a strain of microorganism designated MF 5171 in the culture collection of Merck & Co., Rahway, N.J. and identified as *Zalerion arboricola* and recovering said agent from the culture medium. A sample of the culture capable of producing the Compound IA has been deposited under the Budapest Treaty in the Culture Collection of the American Type Culture Collection at 12301 Parklawn Drive, Rockville, Md. 20852. The sample has been assigned the accession number ATCC 20868.

The colonial and morphological description of ATCC 20868 are set forth below:

A. Morphological description

Globose, approximately 6.0 microns in diameter, thick-walled, dark colored structures similar to chlamydospores develop along mycelium and often appear to be intercalary. These structures appear to divide, forming multi-celled groups of 4–8 cells which do not break up readily. On some media, strands of mycelia cluster together, forming rope-like structures and the multi-celled groups form large clusters as if held together by mucilaginous material.

B. Colonial description

1. Czapek-Dox agar

Colonies are slow growing, growth not extensive, flat with irregular edges. Mycelium is black, shiny; surface becomes dull, granular-appearing, black to greenish-brown as colony ages.

2. Corn agar

Colonies are slow-growing. Growth is not extensive. Mycelium is black, shiny surface becoming powdery, dull black as colony ages.

3. Potato-dextrose agar, Sabouraud maltose agar and yeast extract-malt extract-dextrose agar.

Colonies are slow growing. Growth is not extensive, is slightly raised in the center, radiately furrowed irregular edges except on Sabouraud-maltose agar where the edges are hyaline and regular. Mycelium is black, shiny; becomes dull powder, black as colony ages.

Although the invention is discussed hereinbelow principally with respect to the specific strain, it is well-known in the art that the properties of microorganisms may be varied naturally and artificially. Thus, all strains of the genus ATCC 20868 including varieties and mutants, whether obtained by natural selection, produced by the action of mutating agents such as ionizing radiation or ultraviolet irradiation, or by the action of chemical mutagens such as nitrosoguanidine, are contemplated to be within the scope of this invention.

Compound IA may be produced in a form adaptable for drug use by cultivating the strain ATCC 20868 of *Zalerion arboricola* in a nutrient medium until a substantial amount of antibiotic activity is detected in the culture medium, generally in the mycelium portion thereof, and thereafter recovering the active component from the fermentation mycelium in a suitable solvent, concentrating the solution of active component, and then subjecting the concentrated material to chromatographic separation.

The fermentation is carried out in a medium containing sources of carbon and nitrogen assimilable by the microorganisms and generally low levels of inorganic salts. In addition, the medium may be supplemented with trace metals, although if complex sources of carbon and nitrogen are employed, they are usually present in the complex sources.

The sources of carbon include glycerol, sugars, starches and other carbohydrates or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 5 percent by weight of the medium is satisfactory. These carbon sources can be used individually or several such carbon sources may be combined in the same medium.

The sources of nitrogen include amino acids such as glycine, arginine, threonine, methionine and the like as well as complex sources such as yeast hydrolysates, yeast autolysates, yeast cells, tomato paste, soybean meal, casein hydrolysates, yeast extracts, corn steep liquors, distillers solubles, cottonseed meal, meat extract, and the like. The various sources of nitrogen can be used alone or in combination in amounts ranging from 0.2 to 90 percent by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, iron, molybdenum, zinc, cadmium, and the like.

The media suitable for carrying out the fermentation may be solid or liquid.

Solid media may have a millet, corn, oats, soy bean or wheat base. One medium having a millet base is Medium 2 in Example A. Other representative solid media include the following:

| Media | Weight or Volume Per 250 ml Flask |
|---|---|
| Medium A | |
| Corn (cracked) | 10.0 g |
| Yeast extract | 0.5 g |
| Sodium tartrate | 0.1 g |
| Monosodium glutamate | 0.1 g |
| Corn oil | 0.1 ml |
| Ferrous sulfate · 7H$_2$O | 0.01 g |
| Water | 15–20 ml |
| Medium B | |
| Millet | 15 g |
| Yeast extract | 0.5 g |
| Sodium tartrate | 0.1 g |
| Ferric sulfate · 7H$_2$O | 0.01 g |

| Media | Weight or Volume Per 250 ml Flask |
|---|---|
| Sucrose | 0.5 g |
| Alfalfa | 0.5 g |
| Corn oil | 0.1 ml |
| Water | 15 ml |
| Medium C | |
| Millet | 15 g |
| Yeast extract | 0.5 g |
| Sodium tartrate | 0.1 g |
| Ferric sulfate · 7H$_2$O | 0.01 g |
| Silica gel | 0.5 g |
| Alfalfa | 0.5 g |
| Monosodium glutamate | 0.1 g |
| Corn oil | 0.1 ml |
| Water | 15 ml |
| Medium D | |
| Millet | 15 g |
| Yeast extract | 0.5 g |
| Sodium tartrate | 0.1 g |
| Ferric sulfate · 7H$_2$O | 0.01 g |

In addition, media may be prepared by substituting wheat, barley, oats or soy bean for the millet or corn above.

Liquid media also may be employed. Fermentation on a larger scale is generally more conveniently carried out employing a liquid medium. It has been found that although conventional liquid media may be employed to obtain Compound IA, such media have not been found to be suitable for obtaining good yields of the desired antibiotic. However, by incorporating from about 6 to 9 percent by weight of glycerol, it has been found that good yields of the desired antibiotic compound may be obtained. Suitable liquid media include:

| Medium E | |
|---|---|
| Glycerol | 85 g |
| Pectin | 10 g |
| Peanut Meal | 4 g |
| Peptonized Milk | 4 g |
| Tomato Paste | 4 g |
| Corn Steep | 4 g |
| Lard Water | 4 g |
| Glycine | 2 g |
| KH$_2$PO$_4$ | 2 g |
| Distilled Water to pH 7.0 | 1000 ml |
| Medium F | |
| Dextrose | 10 g |
| Glycerol | 10 ml |
| Soy Flour | 4 g |
| Peptonized milk | 4 g |
| Tomato paste | 4 g |
| Lard water | 4 g |
| Potassium dihydrogen phosphate | 2 g |
| Cobalt chloride hexahydrate | 0.01 g |
| Distilled Water to pH 7.0 | 1000 ml |

For producing Compound IA, a fermentation medium containing ATCC 20868 is prepared by inoculating spores or mycelia of the antibiotic-producing organism into a suitable medium and then cultivating under aerobic conditions.

The procedure generally is first to inoculate a preserved source of culture from an agar slant containing nutrient medium into a nutrient seed-producing medium and to obtain, preferably through a two step procedure, growth of the organisms which serve as seeds in the production of the antipneumocystis agent.

In this process, a slant section of a preserved culture of ATCC 20868 is inoculated into an appropriate liquid nutrient seed medium of pH in the range 5 to 8.1, optimally 6 to 7.5, and the flasks incubated with or without agitation at temperatures in the range of from about 15° C. to about 30° C., preferably 20° to 28° C. Agitation when employed, may be up to 400 rpm, preferably, about 200 to 220 rpm. The incubation is carried out over a period of from 2 to 30 days, preferably 2 to 14 days. When growth is abundant, usually between 2 and 5 days, the culture growth may be used to inoculate the production medium for the production of the antipneumocystis agent. Preferably however, a second stage fermentation is carried out, inoculating with a portion of the culture growth and then employing similar conditions but generally with a shortened incubation period of about 1 to 3 days. The growth then is employed to inoculate the production medium.

The fermentation production medium inoculated with the culture growth is incubated for 3 to 30 days, usually 7 to 14 days with or without agitation. The fermentation may be conducted aerobically at temperatures ranging from about 20° C. to about 40° C. For optimum results, it is most convenient to conduct these fermentations at a temperature in the range of from about 24° C. to about 30° C. Temperatures of about 24°-28° C. are most preferred. The pH of the nutrient medium suitable for producing the instant compounds can vary from about 5.0 to 8.5 with a preferred range of from about 6.0 to 7.5. After the appropriate period for the production of the desired compound or compounds, the latter is recovered from the fermentation medium as hereinafter more fully described.

The active material may be recovered from the fermentation medium by the steps comprising
(1) adding alcohol to said medium, stirring and filtering to recover the active component in the resulting aqueous alcoholic solution;
(2) concentrating the aqueous alcoholic solution to a small volume of primarily aqueous solution;
(3) intimately contacting the resulting concentrated alcoholic aqueous solution with a water-immiscible organic solvent to extract or partition the active component thereinto and concentrating, or subjecting the concentrated solution to HP-20 adsorption and elution; then
(4) subjecting the material recovered in Step (3) to at least one chromatographic separation, wherein in each chromatographic separation, the active component from the eluates exhibiting activity against *Candida albicans* are combined and concentrated to recover Compound IA.

The exact steps may vary somewhat depending on whether the fermentation had been carried out in liquid or solid medium, what solvent is employed and what adsorbent or combination of adsorbents is employed.

When the fermentation is carried out on solid medium, the first step may be carried out by adding an alcoholic solvent to the fermentation medium, thoroughly mixing, then filtering, recovering and concentrating the aqueous alcohol filtrate. Preferably, the concentrated filtrate is first back-extracted or washed with a lower aliphatic hydrocarbon solvent such as hexane or other alkane to remove alkane soluble impurities. The alkane washed filtrate may be extracted or partitioned with a water-immiscible oxygenated organic solvent and the resulting solution concentrated, then placed onto a column for at least one, generally several chromatographic separation steps. Suitable columns are silica gel, reverse phase and "SEPHADEX" LH-20, (dextran gel filtrant, Pharmacia).

When the fermentation is carried out in a liquid medium, in one method, the mycelial solids are filtered and recovered from the fermentation medium. Alcohol is added to the mycelial cake, and the mycelial solid thoroughly mixed with the alcohol, filtered, and the filtrate collected and concentrated. In an alternative method, the whole broth can be extracted by the addition of one volume of alkanol, preferably methanol, and filtered to remove solid impurities. The alkanol extract is then adsorbed on "DIAION" SP-207 (Mitsubishi Chemical Industries) or other commercially available styrene-divinylbenzene copolymer. A second dilution/HP-20 adsorption/elution step is utilized to concentrate the sample in preparation for chromatographic separations. Sometimes, a third dilution/HP-20 adsorption/elution step may be desirable for volume reduction.

The alcoholic solvent to be employed in the initial extraction of the active agent from the solid nutrient medium or from the mycelial pad may be any of the lower alcohols such as methanol, ethanol, isopropanol, and the like. Methanol is preferred.

The water-immiscible non-polar organic solvent useful for extracting or partitioning the active agent from the alkanol or methanol solution are esters, such as ethyl acetate, isopropyl acetate, butyl acetate, or ketones, such as methyl ethyl ketone. Lower aliphatic esters are preferred.

The chromatographic separation may be carried out by employing conventional column chromatography with non-ionic resin or by high performance liquid chromatography employing reverse phase resin. The fractions containing the antibiotic Compound IA may be detected by bioautography using *Candida albicans*. Generally, more than one chromatographic separation steps are employed. In a most preferred procedure, one or more separations are carried out employing column chromatography and a final separation is carried out employing high performance liquid chromatography (HPLC) with $C_{18}$ reverse phase resin.

When conventional column chromatography is employed for chromatographic separations, silica gel is the preferred adsorbent. Usually more than one chromatographic separation is required. Silica gel may be used in all the separations while employing different eluting agents. However, it may be combined advantageously with the use of a different adsorbent such as a dextran gel sold under the trade name of "SEPHADEX" LH-20. Other adsorbents such as alumina, styrene-divinylbenzene copolymers available commercially as DIAION HP-20, HP-30, HP-40, SP-207 and "AMBERLITE" XAD-2, XAD-4, XAD-16 (Rohm and Haas Co.) also may be employed.

In the fractionation and recovery of the active component by chromatography on silica gel, ester/alcohol mixtures with increasing concentration of alcohol provide good separations. A mixture of ethyl acetate and methanol has been found to be especially useful. These may be employed in isocratic, step gradient or continuous gradient systems. When a dextran adsorbent such as "SEPHADEX" LH-20, is employed, a chlorohydrocarbon/hydrocarbon/alcohol solvent system may be employed. A mixture of methylene chloride/hexane/methanol has been found to be especially useful.

In carrying out the HPLC separation, the alcohol solution containing material recovered from the conventional chromatography is concentrated and the residue dissolved in methanol and placed on a column packed with commercial reverse phase resin or on a column filled with silica gel/$C_{18}$ reverse phase resin prepared as amply reported in the literature. Alternatively, the alcohol solution may be diluted to 50 percent with water and pumped onto the column. The column is operated using methane/water (1:1 or optionally other ratios) at 800–2000 psi which produces a flow rate of about 20 ml/min. Separation is monitored at 210 nm.

The fractions are assayed for activity with *Candida albicans*. The product is recovered from the chromatographic procedures by combining the active fractions and concentrating under reduced pressure. The product then may be purified by conventional chromatography or preparative HPLC.

Other natural products which are embraced by the present invention include those which are described in the literature as echinocandins, aculeacins, mulundocandins, athlestain (also referred to as an echinocandin T), sporiofungin or by number designations. The structures in some cases are not completely identified but the compounds are known to be neutral cyclohexapeptides with fatty acid side chain.

The echinocandins include echinocandin-A (also known as A-32204-A) produced by *Aspergillus nidulans-echinulatus* (Swiss patent 568,386); echinocandin-B (also known as A-32204-B and SF-7810-F) produced by *Asp. nidulans* (Swiss 568,386) and *Asp. rugulosus* (Helv. Chim. Acta 62 11252 (1979); German 2,549,127; Belg. 834,289); echinocandin-C (also known as SL-7810-FII) produced by *Asp. rugulosus* (Ger. 2,549,127; Belg. 834,289); echinocandin-D (also known as SL-7810-FIII) produced by *Asp. rugulosus* (Ger. 2,549,127; Belg. 834,289).

Echinocandins B, C and D may be produced together on the fermentations of a strain of *Aspergillus rugulosus*. The major metabolite in the fermentation of *Aspergillus rugulosus* is echinocandin B, having a molecular formula of $C_{52}H_{81}N_7O_{16}$. Echinocandin C and D which are the minor metabolites differ in certain of the amino acids making up the cyclic peptide ring. Thus, echinocandin C, having a molecular formula of $C_{52}H_{81}N_7O_{15}$, contains 3-hydroxyhomotyrosine in place of the 3,4-dihydroxyhomotyrosine present in echinocandin B. Echinocandin D, having a molecular formula of $C_{52}H_{81}N_7O_{13}$, contains 3-hydroxyhomotyrosine and ornithine instead of 3,4-dihydroxyhomotyrosine and 4,5-dihydroxyornithine.

Echinocandin B also may be produced by the cultivation of *Emericella nidulans* as described in the working example.

The aculeacins include aculeacin-A, aculeacin-B, aculeacin-C, aculeacin-D, aculeacin-E, aculeacin-F, aculeacin-G, aculeacin-A A", aculeacin-D A", aculeacin-A G", aculeacin-Aα and Aγ, and aculeacin-Dα and Dγ. The aculeacins may be produced by the fermentation of *Aspergillus aculeatus* (either liquid or solid culture) (preferably M4214 FERM-P 2324) thereafter extracting the mycelium with a water miscible organic solvent concentrating and purifying by chromatography as described in U.S. Pat. No. 3,978,210 and 4,212,858, German Patent 2,509,820 and Belgian Patent 826,393.

Another cyclohexapeptide antibiotic found in the literature is mulundocandin ($R^I$, $R^{II}$, $R^{III}$, $R^{IV}$ are OH, $R^V$ is H, R is —CO(CH$_2$)$_{10}$—CH$_3$CH—CH$_2$CH$_3$) produced by *Asp. sydowic* No. Y-30462 (J. Antibiotics 40, 275 and 40, 281 (1987)). The antibiotic, which is present both in the culture filtrate and mycelium may be isolated from the ethyl acetate extract of a culture filtrate by silica gel column chromatography and droplet counter current chromatography as more fully described by Roy et al, J. Antibiotics 40, 275–280 (1987).

Still another echinocandin type cyclopeptide reported in the literature is sporiofungin ($R^I$, $R^{III}$ and $R^{IV}$ are OH, $R^{II}$ is H, $R^V$ is CH$_2$CONH$_2$, $R^{VI}$ is H and R is a branched chain $C_{16}$ fatty acid radical,) which may be produced by cultivation of Cryptosporiopsis (WIPO publication, WO 82/00587) strain ATCC 20594 or NRRL 12192, on various conventional nutrient media as aerobic surface culture or immersion culture, and the mycelium separated from the culture broth and recovered in a conventional manner such as by homogenizing the mycelium with methanol, extracting from the methanol with a water-immersible organic solvent such as ethyl acetate, removing the solvent and purifying by chromatography as more fully described in WO 82/00587.

Other echinocandin type cyclohexapeptides include X-73 produced by *Aspergillus rugulosus*, (Ind. J. B. Biochem. 7, 81 (1970)), athlestain produced by *Aspergillus niger*, (Jap. J. Ant., 17 268 (1964), JP 66/12688; CA 65 19274; 70, 27607), S-31794-F-1 produced by *Acrophialophora limonispora* (U.S. Pat. No. 4,173,629; Ger. 2,628,965), A-30912-A or A-22082 produced by *Asp. nidulans* and *Asp. rugulosus* (U.S. Pat. Nos. 4,074,246; 4,074,245; 4,288,549; Ger. 2,643,485; CA 87, 20612) A-30912-B, A-30912-C, and A-30912-D, produced by *Asp. rugulosus* (U.S. Pat. No. 4,024,245).

Compounds which are modifications of natural products include those in which the side chain, i.e., R, when an unsaturated fatty acid, had been modified by reduction. This may be carried out catalytically, by using Pd on carbon at atmospheric pressure.

Compounds in which $R^{III}$ is —O-Alkyl ($C_1$-$C_6$) or —O-benzyl may be prepared by stirring together the corresponding compound in which $R^{III}$ is OH with the appropriate alkanol under acidic conditions at ambient temperature for several hours or overnight to obtain the ether in the mixture and thereafter preferably quenching the reaction with dilute bicarbonate and recovering it by conventional procedures. In addition to the preparation in the working example, the preparation for a number of these compounds is more fully described in GB 2,050,385A.

Compounds in which $R^{III}$ is

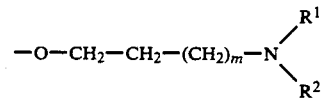

wherein $R^1$ is hydrogen, alkyl or substituted alkyl as previously defined, $R^2$ is hydrogen or $C_1$-$C_4$ alkyl, or $R^1$ and $R^2$ together form —(CH$_2$)$_2$—Q—(CH$_2$)$_2$— wherein Q is a connecting group such as —CH$_2$—, —NH— or —N($C_1$-$C_4$alkyl)—, preferably —CH$_2$—, may be prepared by reacting a compound in which $R^{III}$ formula I in is OH with a compound of the formula

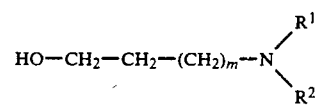

in the presence of an organic acid such as p-toluenesulfonic acid, camphorsulfonic acid, methanesulfonic acid or mineral acid in an aprotic solvent such as dimethylformamide. Preparation of compounds are described in Belgian 851,310. A representative preparation is hereinafter described in the working example.

An especially preferred compound is a compound having a substituent from the foregoing group and represented by the formula

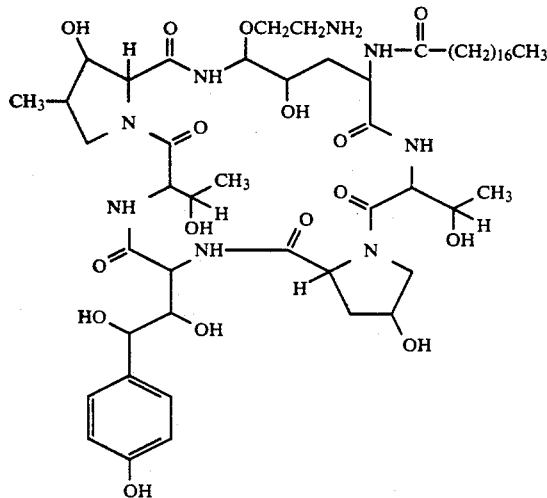

Semi-synthetic compounds in which the acyl side chain, i.e., R in above formula, has been modified from naturally occurring fatty acids to structurally distinctive acyl groups may be produced by first removing the fatty acid side chain and thereafter introducing a distinctive acyl group. The fatty acid side chain preferably is removed enzymatically. The enzyme which is useful for deacylation of the cyclohexapeptides to obtain a cyclopeptide nucleus is that produced by certain microorganisms of the family Actinoplanaceae, especially the microorganism *Actinoplanes utahensis* NRRL 12052 which is available from the Northern Regional Research Center, USDA, Agricultural Research Service, Peoria Ill 61604, or as *A. utahensis* ATCC 14539 obtainable from the American Type Culture Collection, 12301 Parklawn Drive, Rockville, Md. 20852.

The enzyme may be produced by growing Actinoplanaceae at temperatures between about 25° C. and 30° C. and a pH of between about 5.0 and 8.0, preferably between 6.0 and 7.0, with agitation and aeration for from about 40 to about 60 hours in a culture medium containing (a) an assimilable carbon source such as sucrose, glucose or glycerol, (b) a nitrogen source such as peptone, urea or ammonium sulfate (c) a phosphate source such as a soluble phosphate salt and (d) growth promoting inorganic salts.

In the deacylation, the cyclohexapeptide compound or substrate containing the cyclohexapeptide is added to the culture of Actinoplanaceae after the culture has been incubated for at least 48 hours.

After addition of the substrate, the incubation of the culture is continued for about 24 hours or longer over temperatures in the range of from about 25° C. to about 30° C.

The course of the reaction may be monitored by *Candida albicans* assay. The starting cyclohexapeptide compound is active against *C. albicans* but the deacylated nucleus compound is biologically inactive.

The deacylated nucleus compound then may be employed in the preparation of semi-synthetic compounds. Conventional acylation methods may be employed. In one preferred method, a 2,4,5-trichlorophenyl ester of the desired acid is reacted with the deacylated nucleus compound in an inert solvent such as dimethylformamide at room temperature for about 15 to 18 hours. This may be illustrated with a specific example as follows:

A deacylated nucleus of a compound the following structure wherein in formula (IB), E is H (Compound IBi)

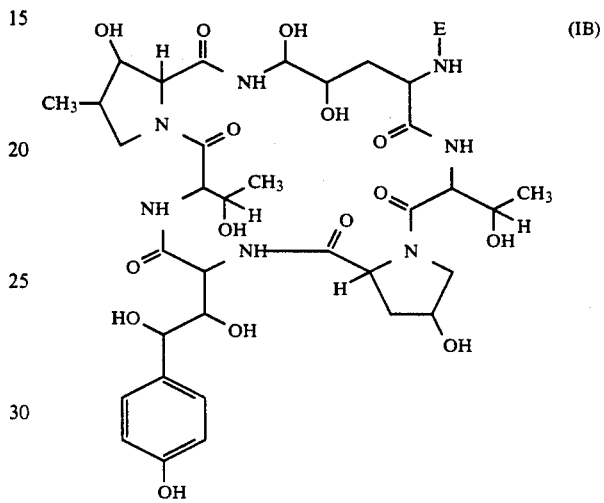

may be prepared by first preparing a deacylating enzyme by the fermentation of *Actinoplanes utahensis* NRRL 12052 by first inoculating a slant with the organism, incubating the slant at 30° C. for about 8 to 10 days and then using the slant growth to inoculate 50 milliliters of vegetative medium which is incubated at 30° C. for about 72 hours with shaking. The incubated vegetative medium may be used to inoculate 400 milliliters of a second-stage vegetative medium having the same composition as the first stage vegetative medium and incubated at 30° C. for about 48 hours with shaking. Thereafter, 800 milliliters of said medium may be used to inoculate 100 liters of production medium which is permitted to ferment at about 30° C. for 42 hours with agitation and aeration to maintain dissolved oxygen level above 30 percent of air saturation at atmospheric pressure and to obtain therein the desired deacylating enzyme.

The medium for preparing the slant may be of the following composition: Baby oatmeal 60.0 g; yeast 2.5 g; $K_2HPO_4$ 1.0 g; Czepek's mineral stock 5.0 ml; agar 25.0 g; deionized water q.s. to 1 liter. Czepek's mineral stock is of the following composition: $FeSO_4.7H_2O$ (in 2 ml. conc. HCl) 2 g; KCl 100 g; $MgSO_4.7H_2O$ 100 g; deionized water to 1 liter with final adjusted pH 6.7.

The medium suitable for both first stage and second stage vegetative medium may be of the following composition: Baby oatmeal 20.0 g; sucrose 20.0 g; yeast 2.5 g; dried grain 5.0 g; $K_2HPO_4$ 1.0 g; Czepek's mineral stock 5.0 ml and deionized water to 1 liter, final pH 6.8.

The production medium may be of the following composition: Peanut meal 10.0 g; soluble meat peptone 5.0 g; sucrose 20.0 g; $KH_2PO_4$ 0.5 g; $K_2HPO_4$ 1.2 g; $MgSO_4.7H_2O$ 0.25 g; tap water q.s. to 1 liter.

An alcohol solution of a cyclohexapeptide (IB) where E is stearoyl (tetrahydroechinocandin B) or palmitoyl (aculeacin A) is added to the production fermentation medium above-described and the deacylation monitored by assay against *Candida albicans*.

On completion of the deacylation, the fermentation broth containing the nucleus compound is filtered, passed through HP-20 resin to place the nucleus compound on the column and the compound recovered by elution with water/methanol (7/3) at a rate of 200–300 ml/minute. The eluate is monitored for the nucleus compound by treating with acid chloride and assaying for activity against *Candida albicans*. The eluate fractions showing activity are concentrated to obtain the nucleus compound (IBi).

The deacylated cyclopeptide compound thus obtained is purified by dissolving in water/acetonitrile/acetic acid/pyridine (96/2/1/1) and purified by reversed phase liquid chromatography ("LICHROPREP" RP-18) at a flow rate of about 60 milliliters per minute and monitoring the separation at 280 nm using a UV monitor. On the basis of the absorption at 280 nm, the fractions containing the desired compound are combined, concentrated under reduced pressure and employed for acylation or lyophilized for subsequent use.

The preparation of the deacylated cyclohexapeptide compound having the same nucleus from echinocandin type natural products is more fully described in U.S. Pat. No. 4,293,482. Similar preparations of other deacylated cyclohexapeptide compounds with similar nuclei may be found described in U.S. Pat. Nos. 4,173,629; 4,293,490; 4,299,763; 4,299,762; and 4,304,716.

The deacylated compounds may then be employed to produce novel and/or unusual acylated compounds.

The acylation of the compound of the deacylated nucleus, to produce a unique acyl derivative may be illustrated with a preparation of a compound in which E in formula (IB) is

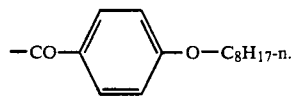
(Compound IBii)

Such a compound would also be illustrative of a compound of formula (I) in which R is a radical defined under (C)(i).

In the acylation, the acyl group is preferably introduced by means of a trichlorophenyl ester. Thus, first, the trichlorophenyl ester may be prepared by treating the side chain acid with 2,4,5-trichlorophenol in the presence of a coupling agent such as N,N'-dicyclohexylcarbodiimide in an inert solvent such as methylene chloride. About 1.1 mole of the 2,4,5-trichlorophenol and 1.0 mole of the coupling agent is used for each mole of the alkoxybenzoic acid. The mixture is stirred at room temperature for 15 to 18 hours to obtain the ester which may be recovered by filtering the solid and evaporating the filtrate under reduced pressure, then recrystallizing the residue.

The ester thus prepared is added to a solution of the nucleus compound in dimethylformamide and stirred for about 18 hours and then the solvent evaporated off. The residue is washed and then chromatographed on silica gel using ethyl acetate-methanol (3/2) as eluant to obtain the desired octyloxybenzoyl derivative which may be represented in formula IB with the octyloxybenzoyl group as E. Such a compound may be named 1-[(4R,5R)-4,5-dihydroxy-$N^2$-[4-(octyloxy)benzoyl]-L-ornithine]echinocandin B (Compound IBii).

In addition to Compound IA, other preferred compounds include Compound IBii; echinocandin B ($R^I$, $R^{II}$, $R^{III}$, $R^{IV}$ are OH; $R^V$ and $R^{VI}$ are CH$_3$; R is

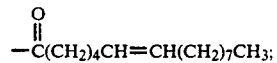

tetrahydroechinocandin B ($R^I$, $R^{II}$, $R^{III}$, $R^{IV}$ are OH; $R^V$ and $R^{VI}$ are CH$_3$; R is

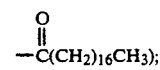

O-methyltetrahydroechinocandin B ($R^I$, $R^{II}$, and $R^{IV}$ are OH; $R^{III}$ is —OCH$_3$; $R^V$ and $R^{VI}$ are CH$_3$; R is

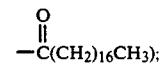

and O-benzyltetrahydroechinocandin B ($R^I$, $R^{II}$ and $R^{IV}$ are OH, $R^{III}$ is —OCH$_2$C$_6$H$_5$, $R^V$ and $R^{VI}$ are CH$_3$; R is

The method of the present invention for the treatment of or for the prevention of *Pneumocystis carinii* infections in mammals comprises administering to subjects infected with or immune compromised subjects susceptible to being infected with *Pneumocystis carinii*, a therapeutically effective or anti-infective amount of a cyclohexapeptide compound represented by Formula I.

The efficacy of the cyclohexapeptide compounds for therapeutic and anti-infective purposes in immune-compromised patients may be determined first in studies on immunosuppressed rats and immunosuppressed mice.

In a representative study employing Compound IA in rats, nine male Sprague-Dawley rats from a colony known to have latent *P. carinii* infections, weighting approximately 200 grams each, were immunosupressed by the addition of dexamethasone to the drinking water (2.0 mg/liter) for six weeks to induce the development of *P. carinii* infections. To enhance the infection the rats were also maintained on a low protein diet. At the beginning of the seventh week the rats were divided into three groups of three rats each. All three groups continued to receive dexamethasone in the drinking water and low protein diet throughout the remainder of the study. The rats in Group I were kept as untreated infected controls, those in Group II were injected intraperitoneally twice daily for two weeks with 0.5 ml of sterile dH$_2$O containing 2 mg of Compound IA, and those in Group III were treated with trimethoprim-sulfamethoxazole (TMP-SMZ) in the drinking water (208 mg TMP and 1.040 g of SMZ/liter) for two weeks, a known treatment for *P. carinii* infections. Two rats died early in the experiment. One was from group II (rat 72A) and the other from group III (rat 75A). It was not determined whether they died from Pneumocystis pneumonia.

At the end of the two week treatment period (a total of eight weeks of immunosuppression) the animals were sacrificed and the lung tissue removed. The lungs from each animal were weighed, and then processed to determine the number of cysts and parasite nuclei for each animal. The results of this experiment are shown in Table I.

TABLE I

IN VIVO TESTING OF COMPOUND IA & TMP-SMZ FOR ACTIVITY AGAINST P. CARINII

| | RAT # | TOTAL CYSTS per lung | TOTAL CYSTS per gm lung | TOTAL NUCLEI per lung | TOTAL NUCLEI per gm lung | LUNG WT. (gms) | CYST SCORE |
|---|---|---|---|---|---|---|---|
| GROUP I (control) | 714 | $3.2 \times 10^8$ | $1.0 \times 10^8$ | $5.8 \times 10^9$ | $1.8 \times 10^9$ | 3.16 | 4 |
| | 74A | $1.5 \times 10^9$ | $4.5 \times 10^8$ | $1.4 \times 10^{10}$ | $4.2 \times 10^9$ | 3.32 | 4+ |
| | 74B | $7.5 \times 10^8$ | $2.1 \times 10^8$ | $1.4 \times 10^{10}$ | $3.9 \times 10^9$ | 3.56 | 4+ |
| GROUP II (COMPOUND IA) | 71B | N.D.* | N.D.* | $2.1 \times 10^9$ | $7.4 \times 10^8$ | 2.83 | 0 |
| | 72B | N.D.* | N.D.* | $1.0 \times 10^9$ | $7.1 \times 10^8$ | 1.40 | 0 |
| GROUP III (TMP-SMZ) | 73B | $6.0 \times 10^6$ | $5.4 \times 10^6$ | $2.0 \times 10^8$ | $1.8 \times 10^8$ | 1.11 | 1 |
| | 75B | $5.4 \times 10^6$ | $2.3 \times 10^6$ | $1.6 \times 10^9$ | $7.0 \times 10^8$ | 2.28 | 1 |

*N.D. = No cysts were detected in 50 fields, indicating that there were less than $2 \times 10^5$ (limits of resolution).

These results demonstrate that Compound IA has efficacy against P. carinii infections. No cysts could be found in the lungs of either rat treated with Compound IA as compared to levels ranging from $3.2 \times 10^8 - 1.5 \times 10^9$ in the control animals. There was also a reduction in the number of parasite nuclei ($1.0 - 2.1 \times 10^9$) in these animals as compared to controls ($5.8 \times 10^9 - 1.4 \times 10^{10}$). These results are superior to those seen in animals treated with TMP-SMZ, a known treatment for P. carinii infections, since the TMP-SMZ rats had detectable levels of P. carinii cysts.

In a repeat experiment with Compound IA, carried out in a similar manner but with larger number of rats and compared with TMP-SMZ and DMSO (solvent) control, it was found that the extent of control of Compound IA and TMP-SMZ was comparable, with the number of cysts per lung being in the DMSO solvent control from $5.8 \times 10^5$ to $3.1 \times 10^7$ for five rats, in the TMP-SMZ treated rats from $3.1 \times 10^3$ to $44 \times 10^4$ for six rats and in the Compound IA treated rats from $3.2 \times 10^3$ to $2.6 \times 10^4$ for five rats. The limit of resolution was $2.8 \times 10^3$.

A similar rat study was conducted to determine the antipneumocystis activity of 1-[(4R,5R)-4,5-dihydroxy-N²-[4-(octyloxy)benzoyl]-L-iiornithine]echinocandin B (Compound IBii). After 6 weeks of immunosuppression the rats were injected twice daily for 7 days with vehicle alone, Compound IBii (2 mg/kg) or Compound IA (2 mg/kg) during which time immunosuppression was continued. At the end of the treatment period the animals were sacrificed and the number of cysts per lung determined. Compound IA reduced the number of cysts by >99% while Compound IBii reduced the cyst counts by approximately 84% (compared to the vehicle control, 10% DMSO).

Studies were also carried out with mice and still other compounds within Formula I. Representative of the method used in the studies carried out with mice and with other compounds is as follows:

Male C₃H/HeN mice, weighing 22-24 grams each, were immunosuppressed by the addition of dexamethasone to the drinking water for six weeks to induce the development of P. carinii infections. To enhance the infections the mice were also maintained on a low protein diet. At the beginning of the seventh week, the mice were randomly divided into groups of 6. All groups continued to receive dexamethasone in the drinking water and low protein diet for the remainder of the study. Mice in each group were injected intraperitonially twice daily with 0.5 ml of a 10% DMSO solution as a vehicle control or the same cocktail containing drug to achieve a dose of 2 mg/kg. This procedure was continued for one week.

At the end of the treatment period (a total of seven weeks of immunosuppression) the animals were sacrificed and the lung tissue removed. The tissue was then processed to determine the number of cysts for each animal.

The results for the various compounds are seen in Table II.

TABLE II

| Compound | Dosage | % Reduction of Cysts |
|---|---|---|
| Tetrahydroechinocandin B (TEB) | 2 mg/kg. | 99% |
| O-Methyl-TEB | 2 mg/kg | >99% |
| O-Benzyl-TEB | 2 mg/kg | 99% |
| Echinocandin B | 2 mg/kg | >99% |
| Compound IA | 2 mg/kg | >99% |

In still another study, the antipneumocystis activity of a compound in wherein $R^I$ is OH, $R^{II}$ is OH, $R^{III}$ is $-CH_2CH_2NH_2$, $R^I$ is OH, $R^V$ is $CH_3$, $R^V$ is $CH_3$, R is

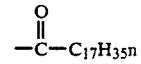

preparation and structure in Example G) was determined. In this study, Sprague-Dawley rats (weighing approximately 250 g) were immunosuppressed with dexasone in the drinking water (2.0 mg/L) and maintained on a regular protein diet for 7 weeks to induce the development of pneumocystis pneumonia from a latent infection. Before drug treatment 2 rats were sacrificed to confirm the presence of Pneumocystis carinii pneumonia (PCP), both rats had infections. The remaining rats (weighing approximately 150 g) were distributed into groups of 6 and injected twice daily for four days subcutaneously with compound in 0.25 ml of vehicle (10% DMSO). The control groups received vehicle alone. All animals continued to receive dexasone in the drinking water and regular diet during the drug treatment period. At the completion of treatment all animals were sacrificed, the lungs were removed and processed, and the extent of disease determined by microscopic analysis of stained slides.

Four dose levels of this compound were tested. The dose levels were 150, 75, 37.5 and 18.25 μg/kg and the results were 99 percent reduction of cysts at the 150 and 75 μg/kg level, 98 percent reduction at 37.5 μg/kg level and 96 percent reduction at the 18.25 μg/kg level. The results indicate an ED₉₀ of below 18.25 μg/kg In a long term (21 days) therapy study, the efficacy of Compound IA was compared to that of two current primary treating agents namely, trimethoprim-sulfamethoxazole and pentamidine. In said study, four treatment periods (4, 7, 14 and 21 days) were compared to determine the relative rate of cyst clearance and the overall reduction of *P. carinii*. Trimethoprim-sulfamethoxazole was administered continuously in the drinking water to achieve at least 2.5 times the recommended human dose (50 mg/kg TMP and 250 mg/kg SMZ). Pentamadine was administered intravenously daily at a dose of 10 mg/kg, 2.5 times the recommended dose for man. Compound IA was given twice daily intraperitonealy at 1.0 mg/kg.

There was rapid elimination of cycts within 4 days with Compound IA while both of the known agents did not show a similar degree of cysts clearance until the two week time point and even then the extent of clearance was not as great as that of Compound IA which was more than a 99 percent reduction. All three agents showed greater than 99 percent reduction at three weeks.

When 4-day treatment experiments were carried out in a similar manner, but using different doses in order to determine the minimum effective dose for 90 percent clearance of *Pneumocystis carinii* cysts, the results shown on Table III were obtained (Six animals were used at each dose level.)

attributable to lack of *P. carinii* organisms and associated inflammation.

TABLE IV

| Agent | No. of rats per group | Cysts+ Log Mean | Reduction | Nuclei+ Log Mean | Reduction | Mean Lung Wt. (gms) | Mean Body Wt. (gms) |
| --- | --- | --- | --- | --- | --- | --- | --- |
| Control | 12 | 7.76 ± 0.10 | | 7.50 ± 0.15 | | 2.53 + 20 | 147.1 ± 6.3 |
| Compound IA | 14 | 4.70 + 0.04 | >99.9%* | 4.85 ± 0.05 | 99.8%* | 1.81 ± .10* | 142.0 ± 4.2 |

*$P \leq 0.002$
+detection limit 4.66; all rats with 0 organisms were scored as 4.66

From the foregoing test results it is determined that generally from about 0.025 to about 20.0 mg/kg of body weight of the cyclohexapeptide anti-pneumocystis agent (Compound I) may be employed while considering the patient's health, weight, age and other factors which influence response to a drug as well as whether it is to be applied to a human patient or to an animal, and whether it is to be for treatment, maintenance or for prevention. These amounts, when expressed as doses suitable for human beings, are in the range of from about 3.5 mg to about 1500 mg daily.

The outstanding properties are effectively utilized when the compound is formulated into pharmaceutical compositions with a pharmaceutically acceptable carrier according to conventional pharmaceutical compounding techniques. It is most effectively utilized in nasal aerosal composition as hereinafter described.

The pharmaceutical compositions contain at least 1% by weight of the active compound. In preparing the compositions, Compound I is intimately admixed with any of the usual pharmaceutically acceptable carriers.

The compositions include compositions suitable for oral, rectal, topical, parenteral (including subcutaneous, intramuscular, and intravenous), and especially pulmonary (nasal or buccal inhalation), nasal administration, or insufflation.

TABLE III

| COMPOUND | $R^I$ | $R^{II}$ | $R^{III}$ | $R^{IV}$ | $R^V$ | $R^{VI}$ | R | $ED_{90}$ mg/kg |
| --- | --- | --- | --- | --- | --- | --- | --- | --- |
| (1) | OH | OH | OH | OH | $CONH_2$ | $CH_3$ | * | 0.2 |
| (2) | OH | H | H | OH | $CONH_2$ | $CH_3$ | * | 1.0 |
| (3) | OH | OH | H | H | $CONH_2$ | $CH_3$ | * | 1.2 |
| (4) | OH | H | H | OH | $CONH_2$ | $CH_3$ | * | <1.0 |
| (5) | OH | OH | OH | OH | $CH_3$ | $CH_3$ | ** | 4.0 |
| (6) | OH | OH | OH | OH | $CH_3$ | $CH_3$ | $-C_{17}H_{35}-n$ | 0.2 |
| (7) | OH | OH | OH | OH | $CH_3$ | $CH_3$ | $-C_{17}H_{31}$ | 1.2 |
| (8) | OH | OH | $OCH_3$ | OH | $CH_3$ | $CH_3$ | $-C_{17}H_{31}$ | <2.0 |
| (9) | OH | OH | $OCH_2C_6H_5$ | OH | $CH_3$ | $CH_3$ | $-C_{17}H_{31}$ | <2.0 |
| (10) | OH | OH | $OCH_2CH_2NH_2$ | OH | $CH_3$ | $CH_3$ | $-C_{17}H_{35}$ | <0.02 |

*9,11-dimethyltridecyl
**n-octyloxyphenyl

In a study to test the effectiveness of these compounds as a potential prophylactic agent, rats with latent *P. carinii* infections were immunosuppressed with dexamethasone in drinking water to stimulate the development of acute PCP. During this immunosuppression period the animals were given daily subcutaneous injections of either 1 mg/kg of Compound IA or vehicle. After six weeks all animals were sacrificed. The number of cysts per lung was determined microscopically and the nuclei (trophozites) were quantitated using a specific DNA probe. From the following table (Table IV) it can be seen that the development of both cysts and trophozoite forms of *P. carinii* is prevented by daily treatments of Compound IA. In addition the lungs in the treated group were significantly lighter in weight The cyclohexapeptide anti-pneumocystis agent, Compound I, may be formulated into compositions for injection and may be presented in unit dosage form in ampoules or in multidose containers, if necessary with an added preservative. The compositions may also take such forms as suspensions, solutions or emulsions in oil or in vehicles such as 20/80 ethanol/propylene glycol or 20-35% polyethylene glycol 300 and may contain formulating agents such as suspending, stabilizing and/or dispersing agents. Alternatively, the active ingredients may be in powder form for reconstituting with a suitable vehicle prior to administration or for use in insufflation.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms measured units in ampoules or in multidose containers and the like. A unit dosage of the present invention will generally contain from 100 to 1000 milligrams of the cyclohexapeptide anti-pneumocystis agent.

Any suitable route of administration may be employed for providing a patient with an effective dosage of a compound of Formula I. For example, oral, rectal, topical, parenteral, ocular, pulmonary, nasal, and the like may be employed. Dosage forms include tablets, troches, disperions, suspensions, solutions, capsules, creams, ointments, aerosols, powders for insufflations and the like.

The compositions include compositions suitable for oral, rectal, topical, parenteral (including subcutaneous, intramuscular, and intravenous), pulmonary (nasal or buccal inhalation), nasal administration, or insufflation.

For administration by the preferred method of inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of Compound I in suitable propellants, such as hydrocarbons and in certain instances fluorocarbons may still be used. Commonly used hydrocarbons are blends of n-butane, propane and isobutane. Cosolvents such as ethyl alcohol may be used.

Because of the difficult solubility of the compound in pharmaceutically acceptable liquid carriers and because of desirability to directly treat lung and bronchi, aerosol administration is an preferred method of administration. Insufflation is also a desirable method, especially where infection may have spread to ears and other body cavities.

Alternatively, parenteral administration may be employed using drip intravenous administration. In such method, the drug may be solubilized in alcohol/propylene glycol or polyethylene glycol compositions. Intraperitoneal injection also may be employed.

The following examples illustrate the preparation of Compound IA and other lipoplilic cyclohexapeptide compound of Formula I and the compositions useful in the present invention of controlling *Pneumocystis carinii* but are not to be construed as limiting.

PREPARATION OF COMPOUND IA

EXAMPLE A

Fermentation

A frozen culture in glycerol of Isolate 2 of Culture 8525-307P originally isolated from water, identifiable as *Zalerion arboricola*, ATCC 20868, and maintained in the Merck culture collection was employed in the fermentation.

A 2 milliliter portion of the frozen culture was defrosted and aseptically transferred to a 250 milliliter unbaffled Erlenmeyer flask containing 54 milliliters of Medium 1. Medium 1, after inoculation, was incubated at 28° C. with rotary agitation (220 rpm, 2" throw shaker) for three days. At the end of this period, 2.0 milliliters of the growth medium were aseptically transferred to each of several unbaffled 250 milliliter Erlenmeyer flasks containing Medium 1. The inoculated flasks were incubated at 28° C. for 2 days.

12.5 milliliters of the mature seed broth were inoculated into five production flasks containing Medium 2, and incubated at 25° C. for seven days under static conditions to obtain an antibiotic compound in the fermentation medium.

The media employed in the foregoing fermentation were:

| MEDIUM 1 (KF Seed Medium) | |
|---|---|
| Corn Steep Liquor | 5 g |
| Tomato Paste | 40 g |
| Oat Flour | 10 g |
| Glucose | 10 g |
| Trace Elements Mix | 10 ml |
| Distilled Water | to 1000 ml |
| pH 6.8 | |
| Trace Elements Mix: | |
| $FeSO_4 \cdot 7H_2O$ | 1 g |
| $MnSO_4 \cdot 4H_2O$ | 1 g |
| $CuCl_2 \cdot 2H_2O$ | 25 mg |
| $CaCl_2$ | 100 mg |
| $H_3BO_3$ | 56 mg |
| $(NH_4)_6MoO_2 \cdot 4H_2O$ | 19 mg |
| $ZnSO_4 \cdot 7H_2O$ | 200 mg |
| Distilled Water | to 1000 ml |

| MEDIUM 2 (F204 Solid Medium) | |
|---|---|
| | Amount/flask |
| Millet Base | 15 g |
| Yeast Extract | .5 g |
| Sodium tartrate | .1 g |
| Ferrous Sulfate Crystals | .01 g |
| Monosodium Glutamic Acid | .1 g |
| Corn Oil | .1 ml |

Isolation

Five hundred milliliters of methanol were added to each of the five 2-liter flasks of solid phase fermentation. The contents of the flask were then combined and stirred to extract methanol-soluble material and the mixture then filtered. The spent cake was stirred with an additional 2500 milliliters of methanol to further extract methanol soluble material and the mixture then filtered.

The filtrate and wash were combined and concentrated to 500 milliliters.

The aqueous methanolic concentrate thus obtained then was extracted with two 500 milliliter portions of ethyl acetate. The spent aqueous solution was placed onto a "DIAION" HP-20 column to adsorb the active material thereon and the latter then eluted therefrom with methanol. The eluates were combined with the previously obtained ethyl acetate extracts and the combined ethyl acetate solutions were concentrated to dryness. The residue was chromatographed on 200 milliliters of "SEPHADEX" LH-20 using 5:5:2 methylene chloride/hexane/methanol as eluant.

The fractions active as determined by *Candida albicans* were combined and chromatographed on 200 milliliters of silica gel (EM Science, "KIESELGEL" 60, 230–400 mesh) using a step gradient elution with ethyl acetate/methanol. The active fractions from this chromatography were combined, concentrated and chromatographed on silica gel using a 75:25 ethyl acetate/methanol isocratic system.

The active portions from this chromatography were then combined and placed on 100 milliliters of "SEPHADEX" LH-20 using methanol as eluting solvent. The eluate, after vaporization off the solvent, yielded 95 milligrams of a purified compound. The compound was a white solid having a $^1$H NMR spectrum as seen in FIG. 1.

EXAMPLE B

Fermentation

In a manner similar to that described in Example A, the contents of one frozen vial of ATCC 20868 from the Merck culture collection were defrosted and aseptically transferred to a 250 milliliter unbaffled flask containing 54 milliliters of KF medium (Medium 1) containing 0.4 percent agar. The modified Medium 1, after inoculation, was incubated at 28° C. with 220 rpm agitation for 48 hours. At the end of this period, 10 milliliters of the growth medium was transferred to a 2-liter unbaffled flask containing 500 milliliters of KF medium containing 0.4 percent agar. After inoculation, the resulting medium was incubated for 24 hours at 28° C. with 220 rpm agitation.

Twenty 2-liter flasks each containing 120 grams of Medium 2 and 120 milliliters of a stock solution consisting of

| Yeast extract | 5 parts by weight |
|---|---|
| Sodium tartrate | 1 part by weight |
| Ferrous sulfate crystals | 0.1 part by weight |
| Monosodium glutamic acid | 1 part by weight |
| Corn oil | 1 part by weight | were autoclaved for 20 minutes at 122° C. and then reautoclaved with 80 milliliters of water for another 20 minutes at 122° C. The flasks were allowed to cool, then inoculated with 20 milliliters of seed medium prepared as above described, and the inoculated flasks incubated at 25° C. under static conditions for 14 days.

Isolation

To each of nineteen 2-liter solid fermentation flasks was added 1 liter of methanol and the contents combined, stirred and filtered. The spent cake was extracted twice with 6 liters of methanol. The aqueous methanol filtrates were then concentrated and the concentrate extracted twice with 3 liters of ethyl acetate. The ethyl acetate extracts were combined, dried and concentrated to about 100 milliliters.

The concentrate was then coated on silica gel by adding 100 milliliters of methanol and 100 milliliters of silica gel thereto, intimately contacting the components and then removing the solvent on a rotary evaporator. The dried silica gel was then applied to a column of 500 milliliters of silica gel, the column washed with ethyl acetate to remove impurities and eluted with 9:1 ethyl acetate/methanol. The eluates containing antibiotic material testing positive against *Candida albicans* were recovered and combined.

The antibiotic rich cut from the silica gel chromatography was dissolved in 200 milliliters of 10:10:1 methylene chloride/hexane/methanol and the resulting solution combined with 40 milliliters of "SEPHADEX" LH-20 (which previously had been prepared by soaking overnight in methanol followed by washing twice with 200 milliliters of methylene chloride/hexane/methanol). After a few minutes, the supernatant was removed by filtration and the "SEPHADEX" LH-20 was washed with 200 milliliter of methylene chloride/hexane/methanol and then filtered. The filtrates were found not to contain the active constituent, and were discarded. The active constituent which had partitioned into the dextran "SEPHADEX" LH-20 beads was extracted therefrom by washing twice with 200 milliliters of methanol, and these methanol washes were combined and concentrated.

The methanol concentrate was next applied to 200 milliliters of silica gel and eluted with 75:25 ethyl acetate/methanol and the eluates combined and the solvent vaporized to obtain Compound IA. Compound IA is a white powder having a decomposition point of 206°–214° C.

PREPARATION OF ECHINOCANDIN B DERIVATIVES

EXAMPLE C

Preparation of Echinocandin B

A. Fermentation

Culture MF 5100 *Emericella nidulans* ATCC 20956 from the Merck culture collection was used for seed train development as follows: One frozen vial (about 2.5 ml) of MF 5100 was used to inoculate 54 mL of KF medium and cultured in 250 ml unbaffled Erlenmeyer flasks at 28° C. and 220 rpm for 72 hours to obtain "B" stage culture. Five mL of "B" stage culture was used to inoculate 500 mL of KF medium in 2 liter unbaffled Erlenmeyer flask and incubated at 28° C. and 220 rpm for 48 hours to obtain "C" stage cultures. Four "C" stage flasks were used to inoculate 160 liters of KF medium with trace element mix #2 in a "D" stage (300 liter stirred fermenter).

The three stages of seed train were used for "E" scale fermentation in an 800 liter fermenter. The fermentation was carried out for 23 hours at 28° C., back pressure 0.7 kg/cm$^2$, aeration with 0.300 m (53 liters per minute) and agitation of 100 rpm.

The production "E" stage was inoculated with 5% seed from "D" stage in 5700 liters of a production medium of the following composition:

| Glycerol | 85 g/L |
|---|---|
| Pectin | 10 g/L |
| Peanut Meal | 4 g/L |
| Peptonized Meal | 4 g/L |
| Peptonized Milk | 4 g/L |
| Tomato Paste | 4 g/L |
| Corn Steep Liquor | 4 g/L |
| Lard Water | 4 g/L |
| Glycine | 2 g/L |
| Potassium phosphate monobasic | 2 g/L |
| Polyglycol P-2000 | 1 mL/L |

The medium was sterilized for 25 minutes at 123° C. and the fermentation then carried out at temperature of 28° C., positive pressure of about 0.8 kg/cm$^2$, aeration 6000 liters per minute, agitation speed of 120 rpm; pH in the range 5.5–6.5 with dissolved oxygen maintained above 30 percent for about 36 hours.

B. Isolation

The whole broth from the above fermentation containing 355 grams of echinocandin B by HPLC assay (against reference standard echinocandin B) was extracted overnight with an equal volume of methanol.

The diluted broth was centrifuged to remove broth solids and the centrifugate adsorbed on a 450 liter SP 207 column which had been equilibrated with 50:50 methanol/water. After a 1000 liter water wash and a 1000 liter 50:50 methanol/water wash, the column was eluted with methanol and the eluate concentrated to 189 liters and partitioned with methylene chloride. The aqueous methanol layer was adjusted to 50:50 methanol/water by the addition of water and absorbed on a 100 liter HP-20 column prewashed with methanol and pre-equilibrated with 50:50 methanol/water. After a 50:50 methanol/water wash, the column was eluted with 80:20 methanol/water. The 80:20 eluate was adjusted to 50:50 with water, and then was adsorbed on a 27 liter SP207 column, preequilibrated as before. The column was then eluted with methanol.

A 19 g aliquot of SP 207 eluate was diluted to 50:50 methanol/water with water and adsorbed on a 3.9 liter "AMICON" preparative C-18 column. A gradient of acetonitrile/water (25:75) to 100 percent acetonitrile over a 75 minute period was used to elute the compound. Selected fraction after concentration and lyophilization from acetonitrile/water provided 16 grams of Echinocandin B of 87-91 percent purity.

The identity and purity of the foregoing echinocandin B was determined by HPLC and spectral comparison with a sample of Echinocandin B, of the properties below, previously prepared and purified, and its identity established by comparison with a published structure of Echinocandin B.

EXAMPLE D

Preparation of Tetrahydroechinocandin B 5.0 Grams of Echinocandin B (EB) of about 87 percent purity (HPLC) was dissolved in 150 milliliters of absolute ethanol and was added to 10% Pd-C in 80 milliliters of ethanol which had been prereduced under 1 atmosphere of hydrogen for 20 minutes. After the addition, the mixture was stirred rapidly under 1 atmosphere of hydrogen for 4 hours. Analysis by HPLC using $CH_3CN/H_2O$ (81/19), on a C8 "ZORBAX" column at flow rate 1 ml/min at 30° C. showed that the reaction was virtually complete at this time.

The reduction mixture was filtered through a "CELITE" pad, the pad washed with ethanol and the mixture was concentrated in vacuo to obtain a solid. The solid was purified in ten 0.5 gram batches dissolved in 5 milliliters of $CH_3CN/H_2O$ (81/19). The HPLC was carried out on C8 "ZORBAX" (DuPont) 1 inch column and eluted with 80% methanol/20% water at a flow rate of 15 ml/min. A total yield of 3.15 grams (79%) of tetrahydroechinocandin B was obtained.

EXAMPLE E

Preparation of O-Methyltetrahydroechinocandin B 55 milligrams of tetrahydroechinocandin B was dissolved in 4 milliliters of methanol. To the solution was added 4.0 milligrams of p-toluenesulfonic acid and the mixture stirred at room temperature for 3 hours. HPLC analysis indicated that the reaction was complete at this time.

The reaction mixture was quenched with 1N sodium bicarbonate solution and washed twice with saturated sodium chloride solution and then diluted with 200 milliliters of isopropanol/chloroform (2/7).

The organic layers were dried over sodium sulfate, filtered and the solvent vaporized to obtain a near white solid as residue. The latter was purified first with methanol, and then with $H_2O/CH_3CN$ (2:3) and chromatographing by MPLC in $H_2O/CH_3CN$ (2:3) on a C8 "LOBAR" size A column in 4 milliliter fractions. The compound was obtained in a yield of 42.4 mg. (76%)

EXAMPLE F

Preparation of O-Benzyltetrahydroechinocandin B 50 milligrams of tetrahydroechinocandin B was suspended in 1 milliliter of tetrahydrofuran. To it was added 97 milliliters of anhydrous benzyl alcohol and the resulting mixture stirred until all was in complete solution. To the resulting solution was added 1 mg. of p-toluenesulfonic acid monohydrate and the mixture then stirred at room temperature for 3 hours whereupon a HPLC analysis showed that the reaction was complete. The reaction mixture was diluted with 1N sodium bicarbonate solution and then with isopropyl alcohol/chloroform (3:7). The organic solution was washed twice with water, dried and evaporated to recover the product as residue.

EXAMPLE G

Preparation of a 2-Aminoethyl ether of Tetrahydroechinocandin B-

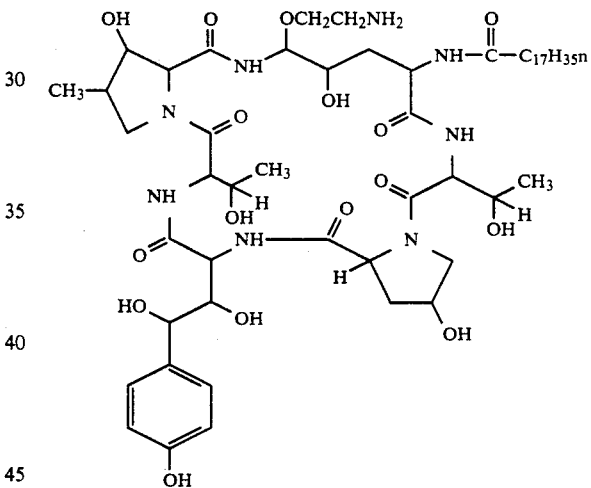

A. Preparation of a (Tetrahydroechinocandin B)-[2-(N-benzyloxycarbonylamino)ethyl ether A solution of 200 mg (0.19 mmol) of tetrahydroechinocandin B, 900 mg (4.62 mmol) of 2-(N-benzyloxycarbonylamino)ethanol, and 43.6 mg (0.19 mmol) of (1S)-(+)-10-camphorsulfonic acid in 20 milliliters of anhydrous dioxane and 2 milliliters of N,N-dimethylformamide was stirred at 25° C. for 16 hours. At this time, the reaction mixture was neutralized with 1M sodium bicarbonate solution and then diluted with 30 milliliters of water. The mixture was then flash chromatographed on EM "LICHROPREP" RP-18 (40–63 μm, 10 gram) packed in 30/70 $CH_3CN/H_2O$ and then eluted with 30/70 to 80/20 $CH_3CN/H_2O$ and eluants concentrated and lyophilized. The impure product from the 80 percent (80/20) fraction after lyophilization was purified by preparation HPLC ("ZORBAX" $C_{18}$ columns, 21.2×250 mm, using 70:30 (containing 0.1% acetic acid) $CH_3CN/H_2O$ as eluant), followed by concentration and lyophilization to obtain 110 milligrams (47 percent) of (tetrahydroechinocandin-B)-[2-(N-benzyloxycarbonylamino)ethyl]ether as a white amorphous powder having the following spectral characteristics.

$^1$H-NMR (400 MHz, CD$_3$OD) $\delta$3.5 (m, 2, OCH$_2$CH$_2$NHZ), 3.6 (m, 2, OCH$_2$CH$_2$NHZ), 5.06 (m, 2 CH$_2$C$_6$H$_5$), 5.14 (d, 1, J=2.7 Hz, H5, H5 4,5-(di-OH)-ornithine), 7.3 (m, 5, CH$_2$C$_6$H$_5$);

FAB-MS (Li), m/e 1248 (M+H+Li)+

B. Preparation of Tetrahydroechinocandin-B, 2-aminoethyl Ether, Trifluoroacetate Salt A mixture of 55 milligrams (0.044 mmol) of tetrahydroechinocandin B, [2-(N-benzyloxycarbonylamino)ethyl]ether, 13 milligrams of 10 percent Pd/C and 10 milliliters of glacial acetic acid was hydrogenated at 1 atmosphere for a period of 16 hours. The mixture was filtered and the filter cake washed with 5 milliliters of acetic acid and 10 milliliters of 50/50 acetonitrile/water. The combined filtrate was concentrated and lyophilized. Preparative HPLC ("ZORBAX" C18, 21.1×250 mm., 65:35 (0.1% CF$_3$COOH) CH$_3$CN/H$_2$O) was carried out on lyophilizate to obtain 20 milligrams (41 percent) of tetrahydroechinocandin B, 2-aminoethyl ether product having the following spectral characteristics.

$^1$H-NMR (400 MHz, CD$_3$OD) $\delta$3.12 (m, 2, OCH$_2$CH$_2$NH$_3$+), 3.73 (m, 2, OCH$_2$CH$_2$NH$_3$+), 5.23 (d, 1, J=2.7 Hz, H5, 4,5-(di-OH)-ornithine);

The following examples illustrate novel compositions useful in the practice of the present invention but are not to be construed as limiting.

Aerosol compositions may be prepared having the following formulations:

EXAMPLE I

|  | Per Canister |
|---|---|
| Compound Ia | 24 mg |
| Lecithin, NF Liquid Concentrate | 1.2 mg |
| Trichlorofluoromethane | 4.025 g |
| Dichlorodifluoromethane | 12.15 g |

EXAMPLE II

|  | Per Canister |
|---|---|
| Echinocandin B | 24 mg |
| Oleic acid | 1.2 mg |
| Trichlorofluoromethane | 4.025 g |
| Dichlorodifluoromethane | 12.15 g |

EXAMPLE III

|  | Per Canister |
|---|---|
| O-Methyltetrahydroechinocandin B | 24 mg |
| Sorbitan trioleate | 1.2 mg |
| Trichlorofluoromethane | 4.025 g |
| Dichlorodifluoromethane | 12.15 g |

An injectible suspension (1M) may be prepared as follows:

EXAMPLE IV

|  | mg/ml |
|---|---|
| Compound Ia | 10 |
| Methylcellulose | 5.0 |
| Tween 80 | 0.5 |
| Benzyl alcohol | 9.0 |
| Benzalkonium chloride | 1.0 |
| Water to 1 ml. | |

General Information For Echinocandin B

*Emericella nidulans* (a later growth stage of *Aspergillus nidulans*, established as a producing organism for Echinocandin B) and maintained as MF 5100 in the Merck culture collection was employed in the fermentation. A culture was deposited with the American Type Culture Collection under the Budapest Treaty and assigned ATCC No. 20956.

Echinocandin B, prepared as described in Example C was compared for percent purity against previously prepared Echinocandin B having the following MS and NMR spectra and identified by comparison with published structure for Echinocandin B.

Mass Spectral Data: FAB mass spectra were recorded on a VG 20-253 mass spectrometer. A matrix of dithiothreitol-dithioerythritol-LiI was used and M+Li was observed at m/z 1066 corresponding to the molecular weight 1059.

Figure 2:
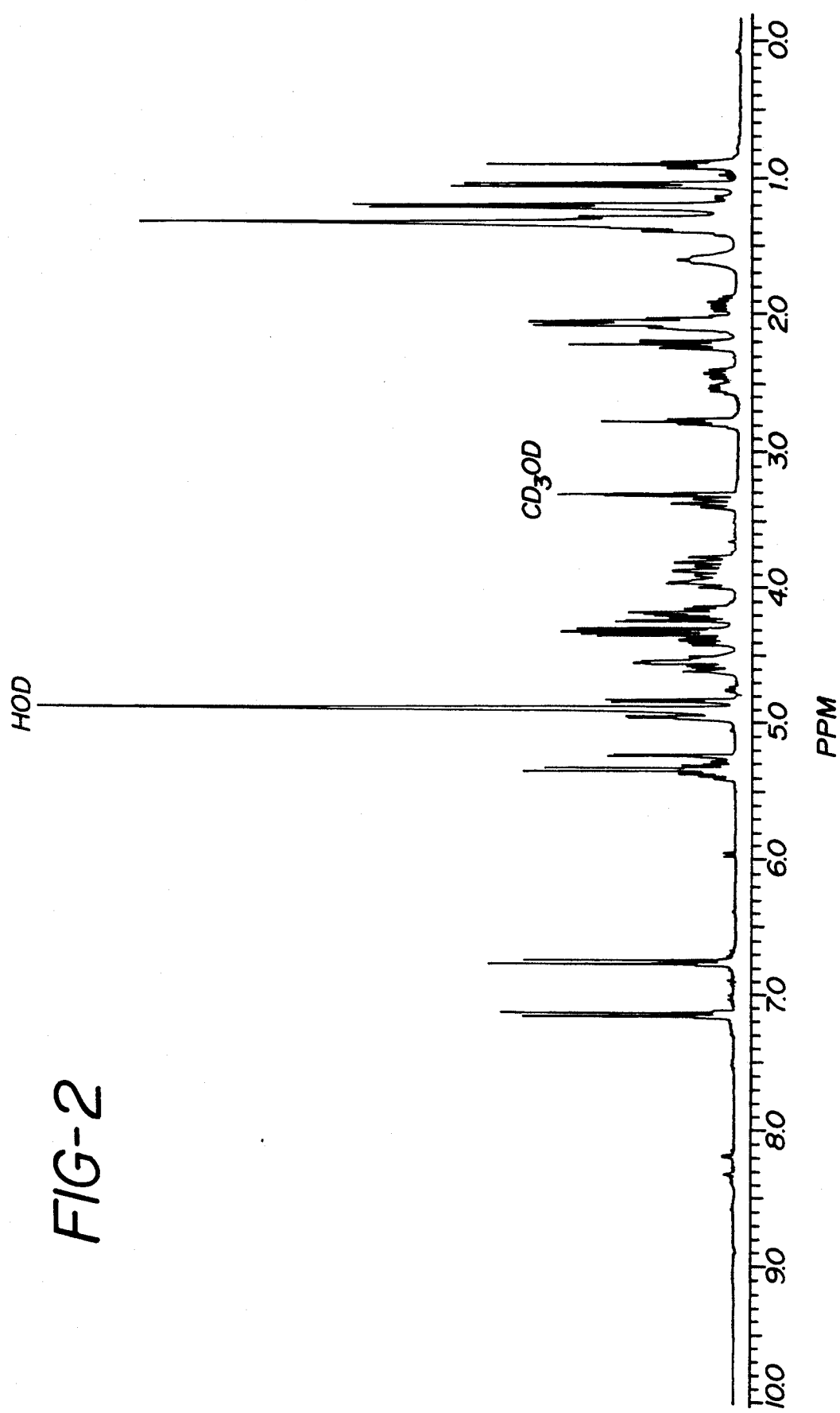

$^1$H NMR Spectrum: The spectrum, FIG. 2, was recorded in CD$_3$OD on a VARIAN XL-300 NMR Spectrometer at 300 MHz. Chemical shifts are shown in ppm relative to tetramethylsilane (TMS) at zero ppm using the solvent peak at 3.30 ppm as internal reference.

$^{13}$C NMR Data: The spectrum was recorded in CD$_3$OD at 24° C. on a VARIAN XL-400 NMR spectrometer at 100 MHz. Chemical shifts are given in ppm relative to tetramethylsilane at zero ppm using the solvent peak at 49.0 ppm as internal reference.

$^{13}$C Chemical Shifts (CD$_3$OD, 100 MHz): 11.28, 14.43, 19.66, 20.04, 23.62, 26.54, 27.05, 28.15, 28.20, 30.27(×2), 30.42, 30.46, 30.78, 32.65, 35.08, 36.82, 38.60, 39.06, 51.67, 52.94, 56.32, 56.84, 57.19, 58.61, 62.46, 68.33, 69.59, 69.70, 70.87, 71.29, 74.60, 75.52, 75.77, 76.94, 116.21(×2), 129.06(×2), 129.60(×2), 130.94, 130.96, 133.09, 158.46, 169.97, 172.48, 172.51, 172.79, 173.53, 174.35, 176.19.

What is claimed is:

1. A method for the treatment of or for the prevention of *Pneumocystis carinii* infections in mammals which comprises administering to mammals an anti-infective amount of cyclohexapeptide compound represented by the formula

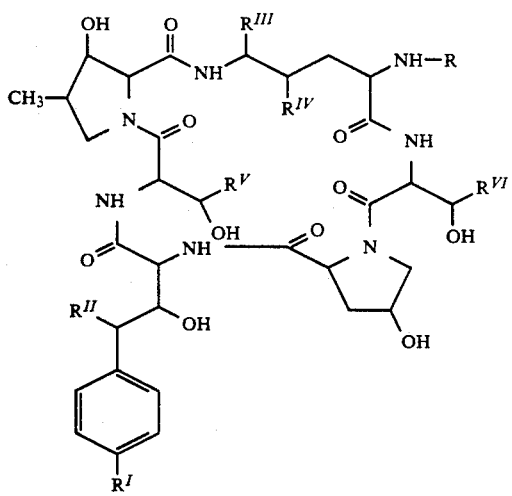

wherein
$R^I$ is OH;
$R^{II}$ is H or OH;
$R^{III}$ is H, OH, —O—($C_1$-$C_6$alkyl), —O-benzyl, or

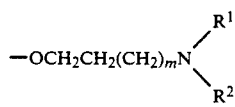

wherein
$R^1$ is H, $C_1$-$C_6$ alkyl, $C_3$-$C_7$ cycloalkyl, hydroxyethyl, ($C_1$-$C_4$ alkoxy)ethyl,
$R^2$ is hydrogen or $C_1$-$C_4$ alkyl; or $R^1$ and $R^2$ together form —$(CH_2)_5$— and m is from 0 to 4;
$R^{IV}$ is H or OH;
$R^V$ is H, $CH_3$ or $CH_2CONH_2$;
$R^{VI}$ is H or $CH_3$; and

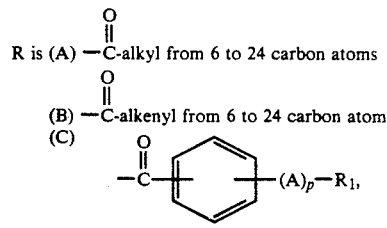

wherein in said (C)
A is divalent oxygen or sulfur,
$R_1$ is hydrogen, $C_1$-$C_{18}$alkyl or $C_2$-$C_{18}$alkenyl;
p is 0 or 1, and provided that $R^I$, $R^{II}$, $R^{III}$ and $R^{IV}$ are OH and $R^V$ and $R^{VI}$ are $CH_3$.

2. A method according to claim 1 wherein the cyclohexapeptide compound is administered at a dose of from 0.5 to 20.0 mg/kg of mammalian body weight.

3. A method according to claim 1 wherein the cyclohexapeptide compound is administered to a patient with an impaired or suppressed immune system infected with or susceptible to becoming infected with Pneumocystis carinii.

4. A method according to claim 1 wherein the cyclohexapeptide compound is administered to a patient with acquired immune deficiency syndrome, infected with or susceptible to becoming infected with Pneumocystis carinii.

5. A method according to claim 1 wherein the compound is that having the formula

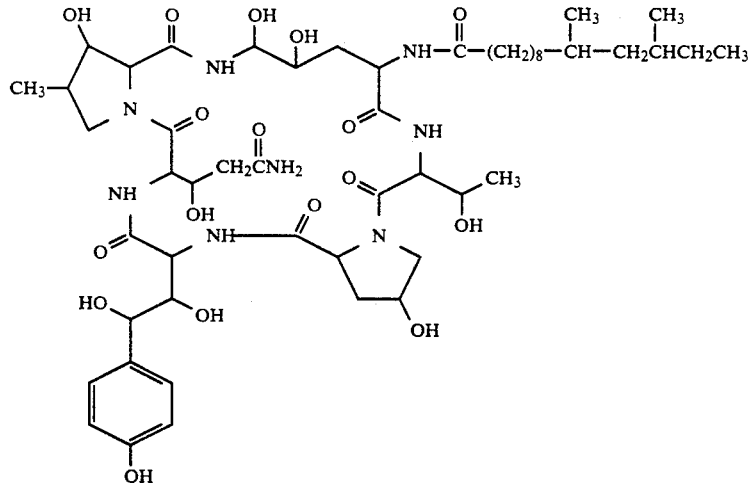

6. A method for reducing or preventing cysts caused by Pneumocystis carinii in immune compromised mammals comprising administering to mammals an effective amount of a cyclohexapeptide compound represented by the formula.

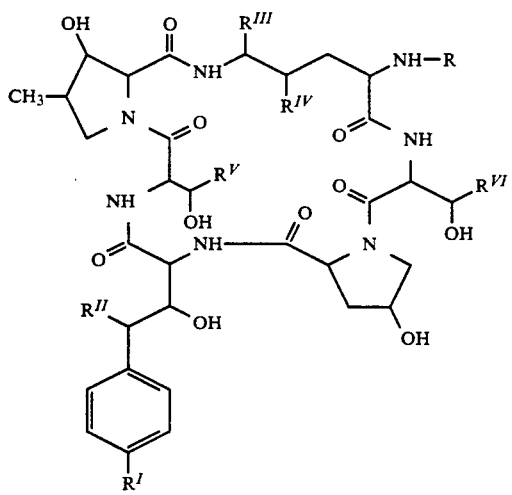

wherein
$R^I$ is OH;
$R^{II}$ is H or OH;
$R^{III}$ is H, OH, —O-alkyl($C_1$-$C_6$), —O-benzyl, or

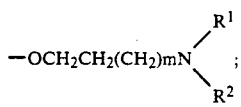

wherein
$R^1$ is H, $C_1$-$C_{16}$ alkyl, $C_3$-$C_7$ cycloalkyl, hydroxyethyl, ($C_1$-$C_4$ alkoxy)ethyl,
$R^2$ is hydrogen or $C_1$-$C_4$ alkyl; or $R^1$ and $R^2$ together form —($CH_2$)$_5$— and m is from 0 to 4;
$R^{IV}$ is H or OH;
$R^V$ is H, $CH_3$ or $CH_2CONH_2$; and
$R^{VI}$ is H or $CH_3$; and $$R \text{ is (A)} \quad \overset{O}{\underset{\|}{-C}}\text{-alkyl from 6 to 24 carbon atoms}$$

$$\text{(B)} \quad \overset{O}{\underset{\|}{-C}}\text{-alkenyl from 6 to 24 carbon atom}$$

(C) 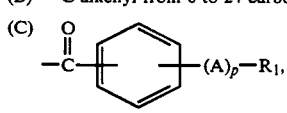

wherein in said (C)
A is divalent oxygen or sulfur;
$R^1$ is hydrogen, $C_1$-$C_{18}$ alkyl or $C_2$-$C_{18}$ alkenyl; p is 0 or 1; provided that $R^I$, $R^{II}$, $R^{III}$ and $R^{IV}$ are OH, and $R^V$ and $R^{VI}$ are $CH_3$.

7. An aerosol composition useful for the treatment of *Pneumocystis carinii* infections in mammals comprising a pharmaceutically acceptable carrier and a cyclohexapeptide compound having the formula

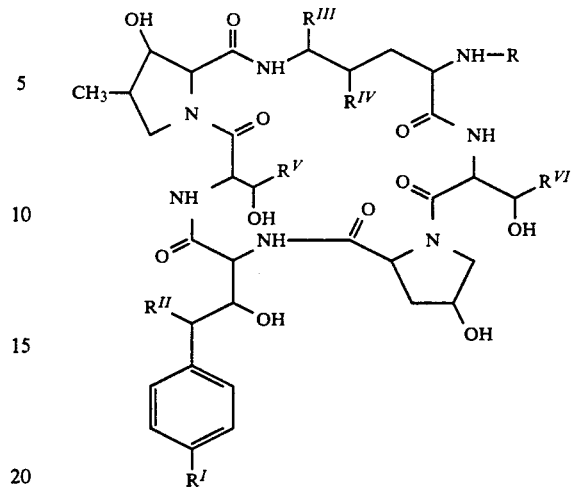

wherein
$R^I$ is OH;
$R^{II}$ is H or OH;
$R^{III}$ is H, OH, —O-alkyl($C_1$-$C_6$), —O-benzyl, or

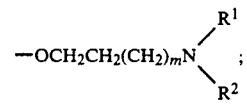

wherein
$R^1$ is H, $C_1$-$C_{16}$ alkyl, $C_3$-$C_7$ cycloalkyl, hydroxyethyl, ($C_1$-$C_4$ alkoxy)ethyl,
$R^2$ is hydrogen or $C_1$-$C_4$ alkyl; or $R^1$ and $R^2$ together form —($CH_2$)$_5$ and m is from 0 to 4;
$R^{IV}$ is H or OH;
$R^V$ is H, $CH_3$ or $CH_2CONH_2$; and
$R^{VI}$ is H or $CH_3$; and $$R \text{ is (A)} \quad \overset{O}{\underset{\|}{-C}}\text{-alkyl from 6 to 24 carbon atoms}$$

$$\text{(B)} \quad \overset{O}{\underset{\|}{-C}}\text{-alkenyl from 6 to 24 carbon atom}$$

(C) 

wherein in said (C)
A is divalent oxygen or sulfur;
$R^1$ is hydrogen, $C_1$-$C_{18}$ alkyl or $C_2$-$C_{18}$ alkenyl;
p is 0 or 1;
provided that $R^I$, $R^{II}$, $R^{III}$ and $R^{IV}$ are OH, and $R^V$ and $R^{VI}$ are $CH_3$.

8. A composition according to claim 7 which is suitable for administration by inhalation.

9. A composition according to claim 7 in unit dosage form.

10. A method for the treatment of or for the prevention of *Pneumocystis carinii* infections in mammals which comprises administering to mammals an anti-infective amount of 1-[(4,5R)-4,5-dihydroxy-N²-(10,12-dimethyl-1-oxotetradecyl)-L-ornithine]-5-(threo-3- hydroxy-1-glutamine)-echinocandin B having the formula tyloxy)benzoyl]-L-ornithine]echinocandin B which has the formula

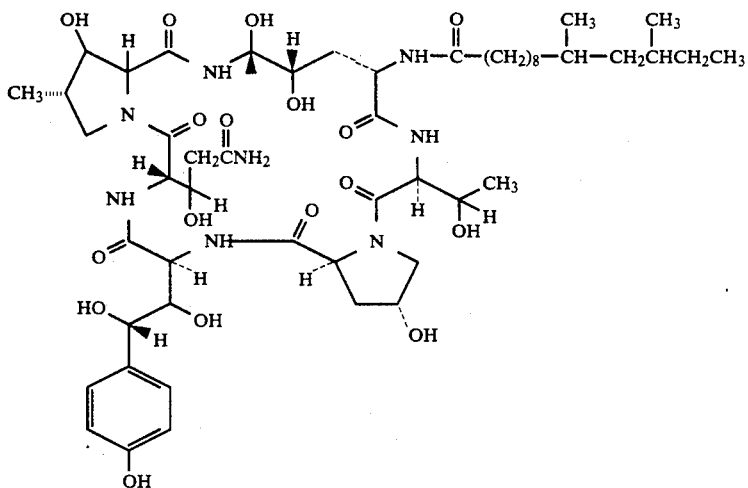

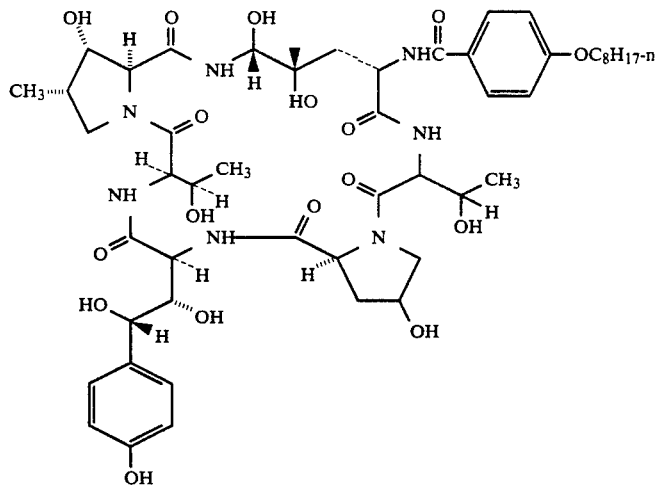

11. A method for the treatment of or for the prevention of *Pneumocystis carinii* infections in mammals which comprises administering to mammals an anti-infective amount of 1-[(4R,5R)-4,5-dihydroxy-$N^2$-[4-(oc- 12. A method for the treatment of or for the prevention of *Pneumocystis carinii* infections in mammals which comprises administering to mammals an anti-infective amount of echinocandin B which has the formula

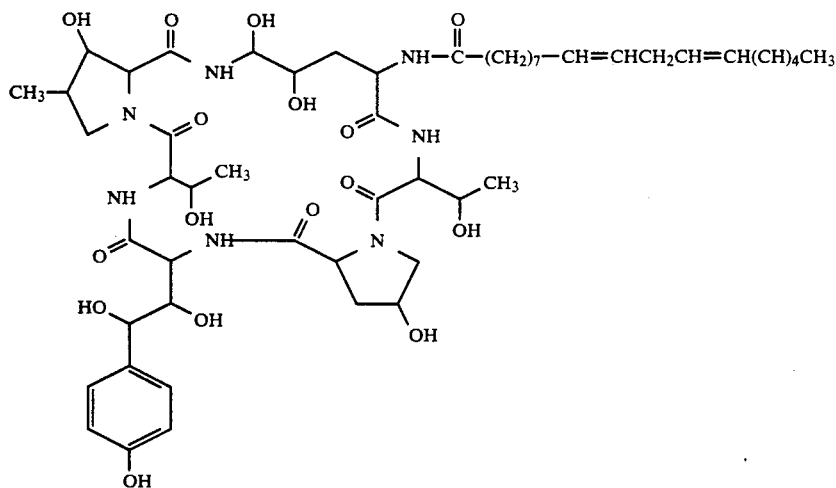

13. A method for the treatment of or for the prevention of *Pneumocystis carinii* infections in mammals which comprises administering to mammals an anti-infective amount of tetrahydroechinocandin B which has the formula

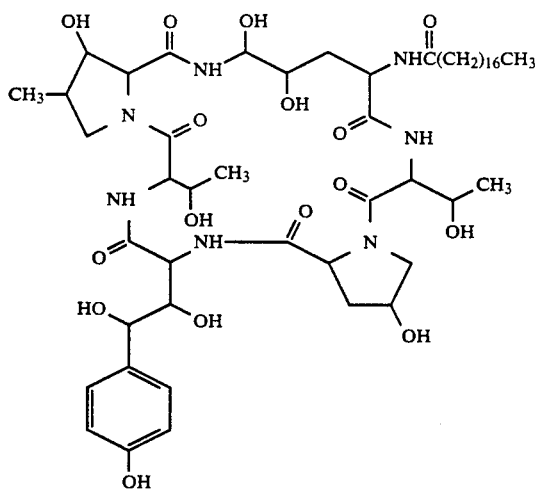

14. A method for the treatment of or for the prevention of *Pneumocystis carinii* infections in mammals which comprises administering to mammals an anti-infective amount of O-methyl-tetrahydroechinocandin B which has the formula

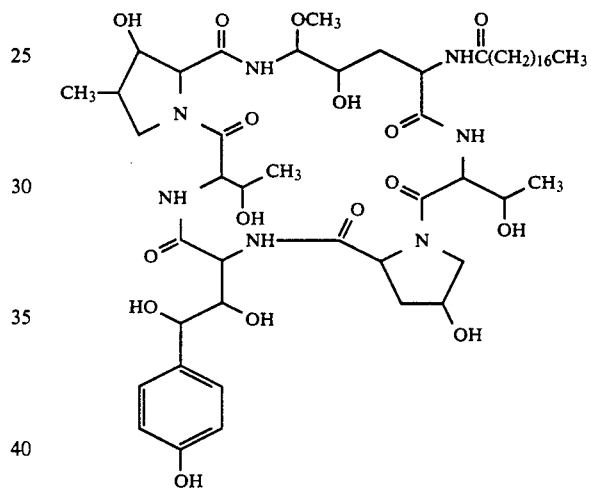

15. A method for the treatment of or for the prevention of *Pneumocystis carinii* infections in mammals which comprises administering to mammals an anti-infective amount of O-benzyl-tetrahydroechinocandin B which has the formula

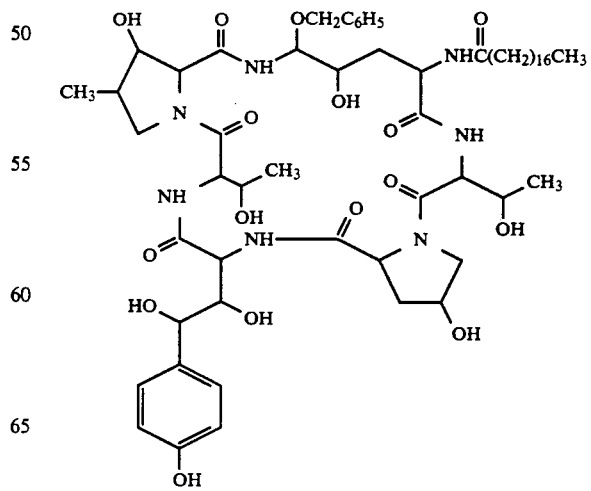

16. A method for the treatment of or for the prevention of *Pneumocystis carinii* infections in mammals which comprises administering to mammals an anti-infective amount of O-(2-aminoethyl)tetrahydroechinocandin B which has the formula
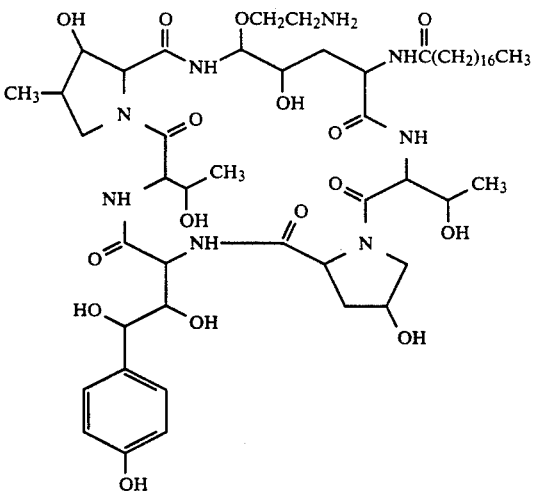
* * * * *